United States Patent [19]
Draper

[11] Patent Number: 6,031,151
[45] Date of Patent: Feb. 29, 2000

[54] CALLUS-SPECIFIC PROMOTERS

[75] Inventor: John Draper, Leicester, United Kingdom

[73] Assignee: The University of Leicester, Leicester, United Kingdom

[21] Appl. No.: 08/199,219

[22] PCT Filed: Sep. 2, 1992

[86] PCT No.: PCT/GB92/01602

§ 371 Date: Mar. 1, 1994

§ 102(e) Date: Mar. 1, 1994

[87] PCT Pub. No.: WO93/05164

PCT Pub. Date: Mar. 18, 1993

[30] Foreign Application Priority Data

Sep. 2, 1991 [GB] United Kingdom .................... 9118759

[51] Int. Cl.$^7$ ............................ C12N 15/29; C12N 15/82; C12N 5/14; F01H 5/00
[52] U.S. Cl. ................... 800/205; 800/250; 800/DIG. 52; 536/23.6; 536/24.1; 435/172.3; 435/419; 435/252.2; 435/320.1; 435/91.1
[58] Field of Search ...................................... 800/200, 205, 800/250, DIG. 52, 53; 536/24.1, 23.6; 435/172.1, 91.1, 172.3, 252.2, 240.48, 240.49, 320.1, 419; 47/58.01

[56] References Cited

U.S. PATENT DOCUMENTS 5,187,073 2/1993 Goldman et al. .................... 435/172.3

FOREIGN PATENT DOCUMENTS 90 13658 11/1990 WIPO .

OTHER PUBLICATIONS

Tada et al. Jul., 1991, The EMBO Journal, 10(7):1803–1808.
Weising et al. 1988, Annu. Rev. Genet. 22:421–477.
Dekeyser, R. et al. "Evaluation of Selectable Markers for Rice Transformation," Plant Physiology vol. 90, pp. 217–233, 1989.
Warner, S.A.J., et al. "Cloning of a Wound Induced Gene from Asparagus–officinalis," Journal of Experimental Botany, vol. 41, 1990, Abstract P5.16.
Warner, S., et al., A Wound–induced Monocot Promoter is Active in Transgenic Tobacco, Journal of Experimental Botany, meeting Apr. 7–12, 1991, vol. 42, 1991, 238 Suppl., p. 37, Abstract P8–11.
Harikrishna, K., et al. "Wound Response in Mechanically Isolated Asparagus Mesophyll Cells: A Model Monocotyledon System," Journal of Experimental Botany, vol. 92, 1991, abstract No. 62138, pp. 791–800.

Primary Examiner—David T. Fox
Assistant Examiner—Thomas Haas
Attorney, Agent, or Firm—Hale and Dorr LLP

[57] ABSTRACT

A marker gene for use in the genetic transformation of plants is driven by a promoter which is capable of acting as a callus-specific promoter, for example in monocotyledonous plants. A suitable promoter naturally drives the expression of a gene encoding a predicted 16.92 kDa protein after wounding and/or callus formation in *Asparagus officinalis* or an equivalent protein in other members of Liliaceae or Amaryllidaceae. A preferred embodiment is designated the AoPR1 promoter. Under the control of a promoter of the invention, the marker gene (which may for example be an antibiotic- or herbicide-resistance gene) is expressed strongly in wounded tissues and cells and cultured explants, but not constitutively throughout the whole plant. Such promoters may also be used to drive expression of genes in plant tissue culture.

23 Claims, 23 Drawing Sheets

| CLONE NUMBER | UPREGULATION IN: | |
|---|---|---|
| | CELLS | WOUNDED PLANT |
| 3 | Y | N |
| 5 | Y | Y |
| 8 | N | N |
| 12 | N | N |
| 16 | RIBOSOMAL CLONE | |
| 17 | RIBOSOMAL CLONE | |
| 18 | N | N |
| 19 | RIBOSOMAL CLONE | |
| 21 | N | N |
| 22 | Y | N |
| 23A | N | N |
| 23B | N | N |
| 27 | N | N |
| 28 | Y | Y |
| 30 | Y | N |
| 33 | RIBOSOMAL CLONE | |
| 34 | Y | N |
| 37 | Y | Y |

FIG.1A

| CLONE NUMBER | UPREGULATION IN: | |
|---|---|---|
| | CELLS | WOUNDED PLANT |
| 38 | N | N |
| 39 | Y | Y |
| | | |
| A5 | N | N |
| A6 | N | N |
| A8 | N | N |
| A9 | N | N |
| A11 | Y | Y |
| | | |
| A12 | Y | N |
| A16 | Y | N |
| A17 | N | N |
| | | |
| Totals (%) | | |
| Up regulated | 11 (39) | 06 (21) |
| Ribosomal | 04 (14) | 04 (14) |
| No signal | 13 (47) | 18 (65) |
| | 28 | 28 |

Y=Yes  N=No

FIG.1B

```
        M   S   S   G   S   W   S   H   E   V   A   V   N   V   A   A   G   R   M   F
  1    ATGAGTTCAGGGAGCTGGAGCCACGAGGTGGCTGTCAATGTCGCCGCAGGACGGATGTTC        60

K   A   A   M   L   D   W   H   N   L   G   P   K   I   V   P   D   F   I   A
 61    AAGGCGGCAATGCTCGACTGGCACAACCTCGGCCCTAAGATTGTGCCTGACTTTATTGCC       120

G   G   S   V   V   S   G   D   D   G   S   V   G   T   I   R   E   I   K   I   N
121    GGTGGCTCAGTGGTCTCTGGAGATGATGGATCTGTAGGAACCATCCGAGAGATCAAGATCAAC     180

N   P   A   I   P   F   S   Y   V   K   E   R   L   D   F   V   D   H   D   K
181    AATCCTGCTATACCTTTCAGCTATGTGAAGGAACGCCTGGATTTCGTAGACCATGACAAG       240

F   E   V   K   Q   T   L   V   E   G   G   G   L   G   K   M   F   E   C   A
241    TTCGAGGTGAAGCAGACACCCTCGTGGAAGGTGGAGGTTTAGGTAAGATGTTTGAATGTGCC     300

T   T   H   F   K   F   E   P   S   S   N   G   G   C   L   V   K   V   T   A
301    ACCACTCACTTCAAGTTCGAGCCCTCGAGCAACGGTGGATGCCTCGTCAAGGTGACTGCA       360

S   Y   K   I   L   P   G   V   A   D   E   S   A   K   A   K   E   G   I   T
361    TCCTACAAGATTCTCCCAGGTGTCGCCGATGAGAGTGCGAAGGCGAAGGAGGAATAACC       420
```

FIG. 3A

```
       N  H  M  K  A  T  E  A  Y  L  L  A  N  P  T  A  Y  V  *  [SEQ ID NO.6]
421  AACCACATGAAGGCAACCGAAGCTTACCTCCTAGCCAACCCAACTGCCTACGTTAAATA  480

481  TAGTGATTGTGTTTCTTTGCCTGAAGTGCTTGTGAGTTTGAATAAGGAGATTGGTTATGA  540

541  GGAAGCTTGATGGGTCATACATAGTTAGTTTATGTTGAATGATCAGCCCTTTTTGTGTG  600

601  AAGTACTTGGGAGTTTGAATAAGGAGACTGAATATGAGAAAGATTGATGGAGTTATCGTT  660

661  CATGTTGAATGATCAGCCCTTATCAGTTTGTAACAGTGTCGAATGATCAGTCTTATCAGTT  720

721  TGTAATGGTGGCCTTCAA  [SEQ. ID. NO: 5]  737
```

FIG.3B

```
  1 GAATTCAGGGGTAAGTTTGCAAATATCAAGATTTGGGGGGCCAAATCTACAAATATGAA  60
 61 ATATTTGAGAGGTATGTATGCAAAAACCCCTATAAATTTCCCTCAGGACTAGACCATCG 120
121 TGGTTAAATGATCAAGTGCCTACTGGCAGAATTTCTTTCGAGCAGCCTCCTCTACAAG  180
181 TTGCATTTGTTGCGCTTACGATAATTGTCAAAGAAGTAGGTAAAATAAAGACATGATCAC 240
241 TAATATTAAGGATAAGATTAAAAATAAGTCCAGGATTAACGGTCGGCCCATCAATTACT  300
301 TGCTGACCTTTGTTGCCGTCCCACGACTTCCATTTCTAACCGTCCATTTTTCATTTGTT  360
361 TTTAGCTATATATTAATATTAATGGATATAAATTATAAACATTCCTCCTCCCAAAAAAT  420
421 AAGTTAAGTAATACTGCAATAGACAGTGTTTTAAGCCATGTAATTCAGTAAAAGTTCTT  480
481 TTTTATTCTGAACCTAGCCCTAAAAAGGCCATGCGGGTAATTAGTTCAGTCAACTGAATA 540
541 TACAACGTTTTGAACCAAAGTTAACATGTACAGGCCAATAGAAGTTATTTGACCGTAAGC 600
601 TTAGTCTCTACATTCATTCAACGTTCTTGAATCAAAGTGACCTGTACAGGCCAATAGAAG 660
661 TTACCTGACCGTAAGCTTAGTCTCTACATTCATTCCTCCTCTGAGACGATATTCTAGAAGCCT 720
```

FIG.5A

```
721  GCTTTCAAGTCTAAAAGGCACAATCTTTTTTCCTCACCACTGTTGAGGTACTTATGATT    780
781  TTAAAGATGAAACATTTTTTTACTTTTCCCCTTAATTCTTTGATTTTTTTTTCT        840
841  GGTAGTTGGAAGTACTTTTCATACCCTAGAAAATCCACTGTTGATCTTTGAAATATCAGC  900
901  AATCTTTGAAATAATATCAGCAACCACGACACCTACCATTCTCAAATTCACTCTATAAAA  960
961  GGGTAAACCCTTTGCTTACCTCTATGCTCACTCACAAGGAGAACAAACACTCATGGTGCT 1020
          M  S  S  G  S  W  S  H  E  V  A  A  N
1021 ACATAACAACAGAGAGGAAACATGAGTTCAGGGAGCTGGAGCCACGAGGTCGCTGCCAAT 1080
      V  A  A  G  R  M  F  K  A  A  M  L  D  W  H  N  L  [SEQ. ID NO:8]
1081 GTCGCCGCAGGACGGATGTTCAAGGCGGCACTGGACTGGCACAACCTCG [SEQ. ID. NO:7] 1132
```

FIG. 5B

```
1042 ATGAGTTCAGGGAGCTGGAGCCACGAGGTCGCTGCCAATGTCGCCGCAGG 1091  IPCR AoPR1PROM
     ||||||||||||||||||||||||||||||| |||||||||||||||||||
   1 ATGAGTTCAGGGAGCTGGAGCCACGAGGTCGCTGTCAATGTCGCCGCAGG   50  AoPR1 cDNA

1092 ACGGATGTTCAAGGCGGGCAATGCTCGACTGGCACAACCTCG 1132
     ||||||||||||| ||||||||||||||||||||||||||||
  51 ACGGATGTTCAAGGGGGGCAATGCTCGACTGGCACAACCTCG   91

FIG.6
```

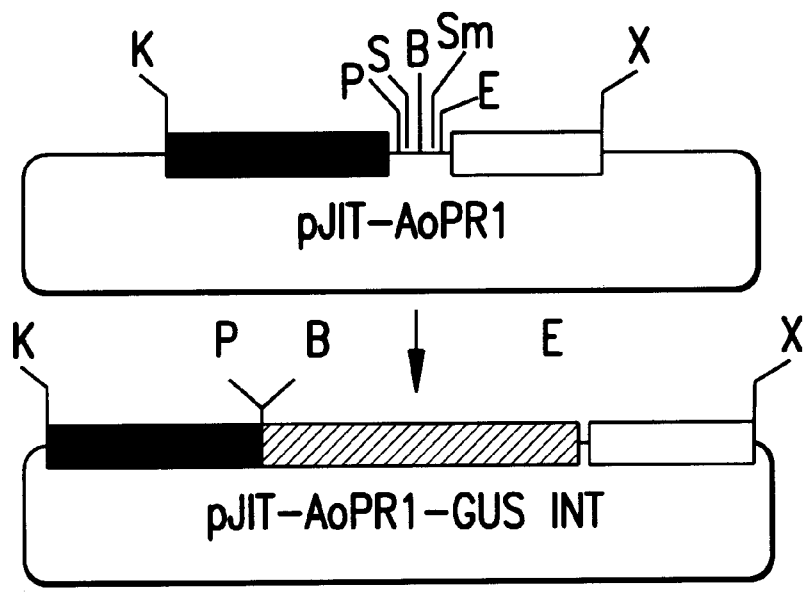
| | AoPR1 PROMOTER | K = KpnI | B = BamHI |
| :-: | :- | :- | :- |
|  | | P = PstI | Sm = SmaI |
|  | GUS INT | S = SalI | E = EcoRI |
|  | CaMV POLY A | X = XhoI | |
FIG. 12B

CALLUS-SPECIFIC PROMOTERS

FIELD OF THE INVENTION

This invention relates to the application of recombinant DNA technology to plants and plant cell cultures. Specifically, the invention relates to the control of the expression of genetic transformation marker genes with the aim of improving transformation systems and of reducing the unwanted expression of marker genes in transgenic plants. The invention therefore enables the provision of more environmentally and nutritionally acceptable genetically engineered crops and foodstuffs. By enhancing gene expression in plant cell cultures, the invention additionally enables or improves the production of compounds in plant cell culture.

BACKGROUND OF THE INVENTION

The aim of crop plant genetic engineering is to insert a gene (or genes) which improve what may be an already top performing plant variety whilst retaining the desirable genetic make up of the original plant. This technology can be integrated into traditional plant breeding programmes and apart from extending the potential genetic make-up of crops to include genes outside the normal gene pool, or synthetic genes, the process for introduction of new genetic information is rapid, much more precise and avoids the lengthy backcrossing programmes usually associated with the introgression of a gene via sexual crossing.

Genetic transformation is a relatively rare event and so most strategies for gene transfer into plants require the use of a transformation 'marker' gene in order to 'select' or 'screen' for transformed plant material. Conventional marker genes are usually microbial in origin and include antibiotic resistance genes, herbicide resistance genes and genes coding for easily screenable enzymes. Transformed plant material are thus 'selected' by an ability to grow in the presence of normally toxic levels of specific antibiotics or herbicides, or 'screened' for by assaying for the expression of novel enzymatic activities not normally found in higher plant tissue.

The expression of marker genes is crucial only at phases of the gene transfer process when transformed cells/tissues/organs or whole plants are being selected or screened for. However, these marker genes are invariably under the control of strong, constitutive gene promoters (for example the Cauliflower Mosaic Virus 35S promoter) which drive marker gene expression in almost all tissue types at high levels throughout the life cycle of the plant. Although much effort has gone into the development of new marker genes, sufficient attention has not been paid to the specific control of marker gene expression. Improvement in the utility of marker genes, since their conception in 1983, has been very slight and has been concerned mainly with attempting to increase the levels of their expression.

One drawback of many marker genes is that they generally show poor expression in monocotyledonous cell types, particularly cereals, and one aim of this invention is the specific development of marker genes that function efficiently in monocot cells.

This invention relates to the improvement of transformation vectors and transformation procedures by engineering marker genes for their strong expression specifically in cell types which are targets for gene transfer. The invention also relates to ensuring or helping ensure strong gene expression in transformed cells at stages in the transformation process when selection is applied.

The invention further relates to enabling or improving the strong expression of genes in plant cell cultures, thereby enhancing the quantity or quality of the direct or indirect product of the genes. Direct products of genes are proteins (which term includes glycoproteins when the context so admits); indirect products of genes include non-proteins when the direct product is an enzyme.

The invention still further relates to the inducible expression of marker genes in transformed plant material to allow the application of more stringent selection conditions and to allow screening for a transiently inducible transformation marker phenotype in established transgenic shoots or transgenic plants at any stage in their life cycle.

To simplify plant breeding strategies it is preferable to obtain transgenic plants with only one copy of an inserted gene and accompanying selection marker gene. In many species, transgenic plants can only be recognised using high concentrations of selective agents. A current problem is that transgenic plants recovered from transformation processes using high levels of selective agents often contain multiple copies of the transferred DNA. It is postulated that high levels of marker gene expression are required to obtain transformants in this situation. A further aim of this invention therefore relates to the specific engineering of marker genes to drive high expression levels in transformed plant cells to allow transformants to be generated with a minimal number of copies of the transferred DNA.

The expression of transformation marker genes is not a required or indeed desirable feature of any improved plant variety. High level marker gene expression is common in transgenic plants. In commercially grown crops this gene expression represents a drain on plant resources to manufacture unwanted proteins and may result in yield depression. Moreover, the presence of large amounts of plant material containing particularly enzymes which inactivate antibiotics normally used to treat human and animal infections is certainly an undesirable feature of most foodstuffs currently derived from genetically engineered plants. Thus, a further aim of this invention is the manipulation of marker gene expression to minimise as much as possible marker gene products in commercially grown crop plants.

SUMMARY OF THE INVENTION

At its broadest, the invention is based on the realisation that by selecting a promoter of appropriate specificity, it is possible to use marker genes to monitor the plant transformation process without the drawback of having the marker gene continue to be expressed throughout the life of the transformed plant. It has also been realised that appropriate promoters exist in nature.

BRIEF DESCRIPTION OF THE FIGURES

FIG. 3 shows the DNA sequence of the AoPR1 cDNA (SEQ ID No:5) together with the deduced protein sequence (SEQ ID No:6) of the ORF contained in the *Asparagus officinalis* AoPR1 cDNA.

FIG. 5 shows the nucleotide sequence (SEQ ID No:7) of the *Asparagus officinalis* gene promoter with predicted coding sequence (SEQ ID No:8).

FIG. 6 shows an alignment of the *Asparagus officinalis* AoPR1 cDNA and the AoPR1 gene PROM fragment.

FIG. 12b shows the construction of an AoPR1-GUS-INT transformation vector.

DETAILED DESCRIPTION OF THE INVENTION

Figure 2A:
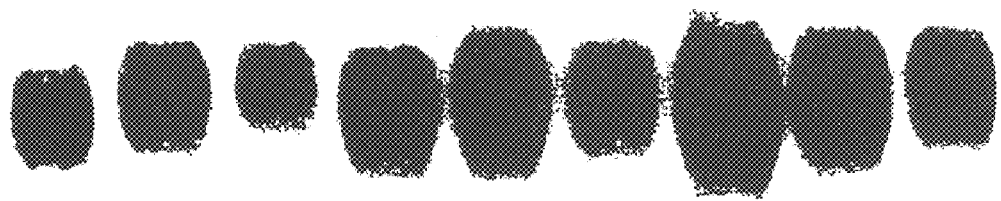
FIG. 2a shows Northern analysis of transcript following cell isolation and wounding.

According to a first aspect of the invention, there is provided an isolated or recombinant DNA molecule comprising a sequence capable of acting as a promoter in callus cells of or from a monocotyledonous plant.

Callus may be defined, for the purposes of this invention, as a mass of cells formed by plants over or around a wound. Such cells may generally be parenchymatous. It is promoters which are active in such cells in monocotyledonous plants which are useful in this aspect of the invention, because it surprisingly appears that they are useful to drive expression of genes in both monocotyledonous and dicotyledonous plant cells. The promoters are also useful in driving gene expression of plant cells in culture, particularly callus-derived cells; the culture may be a tissue culture or a cell culture.

Promoters useful in the invention are active in callus cells, and generally preferentially in callus cells. They may additionally be largely or essentially specific for callus cells, although some expression in other cells of a plant may be tolerated or even desired for some purposes. Generally, though, expression will be stronger in callus cells, whether in the plant or in culture, than in other cells of the plant.

An important consideration relating to this invention is the specification of cell types in which marker gene expression is required to achieve gene transfer to plants; thus two major aspects of the utility of this invention are to achieve strong marker gene expression specifically in such cell types and indeed to limit marker gene expression mainly to these cell types. By means of the invention, the expression of genes in dedifferentiated tissue can also be exploited to enhance the recovery of products from plant cell cultures. The genetic engineering of plants or plant tissue relies on an ability to integrate an exogenous gene (or genes) stably into the nuclear genome of a plant cell and then to force the transformed plant cell, or cells derived from the original transformed cell, to regenerate into a whole plant. This procedure will be referred to as genetic transformation (or transfection) and is usually, but not exclusively, carried out under sterile conditions using cell/tissue culture techniques on wounded plant material which will be referred to as explants.

Explants, as the term is used in this specification, range from single cells or protoplasts to large organ (eg. leaf, hypercotyl or root) sections or whole seedlings. On appropriate tissue culture media, callus formation can ensue from explants at wound sites by appropriate manipulation of the medium (often by including appropriate relative concentrations of auxins and cytokinins in the medium) and it is possible to regenerate plants from callus-derived cells. Plant regeneration is achieved either via shoot organogenesis or by somatic embryogenesis. In the case of organogenesis the regenerated shoots normally have to be separated from the parent callus and adventitious root production induced at the base of the shoot, often on a different medium designed for the purpose. It should be noted that induction of adventitious cell division and shoot or somatic embryo can also occur in some tissue cultured explants at sites not necessarily associated with the original wound site and that plant regeneration does not always occur via discernible callus phase. For example it is possible to derive whole plants directly from immature pollen grains of several species. The origin of adventitious shoots and somatic embryos is not clear but it is thought that primordia giving rise to these structures are derived from single 'totipotent' cells.

Totipotent cells may be defined as cells which have the capacity to regenerate directly into, or produce, cells that will give rise to a whole new plant via embryogenesis or organogenesis. Such cells represent targets for gene transfer into plants by a variety of techniques. The transfer of genes into target plant cells in explants can take place by means of any suitable method and is commonly achieved by well described methods involving either Agrobacterium vectors or physical DNA delivery techniques such as microprojectile bombardment, microinjection or electroporation.

To achieve the production of a transformed plant, the target plant cells must be 'competent' for both transformation and capable of giving rise to regenerated plants. In addition such cells have to be physically accessible to the transforming vehicle (eg Agrobacterium) or accessible by any physical transformation technique. The problem of accessibility usually limits gene transfer to target cells that are close to the surface of the explant which will often represent a wounded region of the explant. Cells accessible to the transformation technique which also exhibit both competence for transformation and totipotency are rather rare in any explant and are most commonly associated with regions close to the cut surface (the wound site) in any explant.

The control of cellular competence for genetic transformation and totipotency is not understood. However there is much circumstantial evidence to suggest that mechanical wounding and the dedifferentiation and induction into cell division of cells local to the wound site plays an important role in transformation by Agrobacterium. Similarly, the integration of exogenous DNA by plant protoplasts probably occurs only in cells undergoing a similar dedifferentiation and reactivation of the cell cycle. Other totipotent target cell types for transformation, particularly by microprojectiles, Agrobacterium or microinjection are often already dedifferentiated and dividing single cells (often derived from protoplasts), callus or established suspension cultured cells. In several cases it has been demonstrated that cells in immature plant organs (for example, embryonic tissues, embryos, seeds, germinating seeds, apical shoot meristems and axillary bud meristems) can be transformed by well described techniques. Such cells may divide, without undergoing dedifferentiation and callus formation, during the normal development of the organ concerned and can establish plants chimeric for transformed cell lineages from which it is possible to rescue whole transformed plants by a variety of well established techniques. For example, if transformed cell lineages give rise to gametes then transformed seedlings can be recovered in the next generation.

Transformed plant material is normally selected by an ability to grow on a medium containing selective agents and several strategies are commonly employed. For example, transformed callus, or cell colonies derived from single cells or protoplasts, continuing to grow in the presence of selective antibiotics or herbicides may first be established on a callusing medium and then transformed shoots may be derived from such callus by transfer to a shoot regeneration medium. Alternatively, in carrot for example, transformed embryos may be regenerated directly from transformed proembryogenic material and whole plants developed directly in the presence of selective agents. In many plant species (for example tobacco) it is possible to produce transformed shoots directly from wound sites on organ explants on shoot regeneration media which allow only a very limited amount of callus formation. In transformation protocols which generate chimeric transformed plants (for example microprojectile bombardment of shoot primordia, axillary or apical meristems, zygotic or somatic embryos or embryogenic cell lines) it is possible to regenerate whole transformed plants from tissue containing transformed cell lineages, or it is possible to select wholly transformed seedlings in the second generation of seedlings derived from an original chimeric transformant, by their ability to grow on media containing selective agents. The transformed nature of shoots, embryos or seedlings resulting from any protocol can normally be confirmed by their ability to root and grow in the presence of selective agents or by screening for the expression of any particular marker genes.

For the purpose of the present invention, marker gene expression is desirable in the following generalised cell types (shown in Table 1) when selection is applied or screening for the presence of marker genes is desired, although it is recognised that this is not an exhaustive list.

Table 1

Target Cells for Gene Transfer and Selection

1) Cells undergoing cellular dedifferentiation which eventually give rise to callus or directly undergo organogenesis or embryogenesis;

2) Cells contained within callus, or within cell colonies derived from single cells or protoplasts or cells within cell suspension cultures;

3) Cells which give rise to transformed shoot or root primordia or somatic embryos;

4) Cells contained within developing roots, shoots, embryos or seedlings growing in the presence of selective agents;

5) It is also desirable to allow transient, inducible marker gene expression to allow the screening for transformed plants in small tissue explants taken at any stage of the life cycle.

The promoter is that region of a gene which regulates its expression, for example by specifying the time or location of expression, or gene expression in response to a particular stimulus, such as wounding or pathogen attack. Promoters can be separated from the coding region of a gene and used to drive expression of a different coding region, thus allowing the expression of a different product. A promoter can in principle be used to control the expression of any gene and limit the production of its gene product to specific cell types during development or allow production of the gene product under specific environmentally inductive conditions or in response to applied stimuli.

The invention is based in part on the realisation that appropriate genes can be isolated as sources of promoters that will allow the desired controllable expression of genes in plant tissue culture and of marker genes in the cell types defined above both to improve transformation procedures and improve the quality of transgenic crop plants. After isolating appropriate genes the promoter region could be identified and used to develop new marker genes strongly expressed in the desired cell types but with a very controllable expression profile. Desirable features of such a promoter include that fact that it will drive high expression in vitro in any plant species in target cell types appropriate for transformation and in appropriate cell types when selection for transformed material is applied. A second desirable feature of such a promoter is that it will not allow gene expression in the majority of cell types in plant material grown outside of tissue culture. A third desirable property of the promoter is for it to be inducible in any cell type by an exogenous stimulus to allow the general expression of marker genes when required for screening or selection. It is recognised that the marker genes presented as examples in this invention are not an exhaustive list and that may other types of screening or selective markers can be used. A fourth desirable property of such a promoter is that it will allow the strong expression of a marker gene in monocotyledonous cells. Promoters useful in the present invention have at least some, and preferably all, of these desirable properties.

It is also clear that the promoters described could be used to control the expression of any other genes in the cell types described, or after applying an appropriate stimulus, to improve crop plants in many other conceivable ways. For example the induction of gene expression specifically at plant wound sites could be used in strategies aimed to engineer plant resistance to pathogens. It is also clear that the systemic induction of gene expression by chemical elicitors would allow the production in crop plants of specific commercially valuable, protein products in a controllable fashion.

The expression of genes in tissue culture can also be exploited to enhance the recovery of products from plant cell cultures. A gene involved in the production of a compound, when driven by such a strong promoter, might be expected to enhance the recovery of product above levels achievable either by selection of cell lines for high product levels or by the introduction of genes driven by other promoters less strongly expressed in culture.

The induction of cell division and callus formation at wound sites is typical mainly of dicotyledonous plant tissue and is not exhibited by most monocotyledonous plants (eg. cereals) notably with the exception of certain members of the family Liliaceae (eg. asparagus). In most plants the wound callus is short lived as the callus cells quickly become impregnated with suberins, lignins and other water-impermeable substances which seal the wound site and form the 'wound boundary layer'. One component of the plants response to mechanical wounding (and also pathogen invasion) is the rapid induction of transcription of a range of 'defence'-related genes. These genes may be activated in cells very close to the wound site (or site of pathogen invasion) or may be activated systemically in wounded/infected plants (or in some cases both), depending on the severity of wounding. The transcription of many of these 'defence' related genes can also be upregulated by treatment of plants, or parts of plants, with 'elicitors' of biological origin (eg. fungal cell wall fragments) and non-biological origin (eg. salicylic acid, arachidonic acid or glutathione). Such genes expressed in viable cells close to the wound site and during subsequent callus formation from such cells may provide promoters which are useful in the present invention and which can limit gene expression to sites in explanted plant tissue where transformation takes place. Additionally, it is possible that such promoters may be inducible by chemical elicitors.

It is very difficult to study viable cells at a plant wound surface, or cells giving rise to wound associated callus, as such cells are surrounded by non-wounded tissue. To circumvent this problem, the majority of studies in the past leading to the cloning of 'defence' related genes were undertaken by identifying cDNA clones specific to mRNA induced specifically by 'elicitor' treatment in long term suspension cultured cells. However, it is not really clear if already dedifferentiated, dividing, cultured cells treated with elicitors represent a good model for the behavior of genes at the wound surface of explants following excision from plants and placement into tissue culture. It is important to make this distinction as it is well recognised that plant explants are competent for transformation by Agrobacterium 2–4 days post-wounding and selection for transformed cells is only imposed after this time period; therefore any marker gene must be active at the wound site during this period of time.

Many 'defence' related genes so far studied are induced within 20–30 min post wounding/elicitation/infection and their expression is only rather transient, reaching a peak several (6–8) hours after initial induction. For example, promoters of several 'defence' related genes (eg. PR2 of parsley, Chs-8 and PAL of bean and PR1 of tobacco) have been identified and shown to be capable of driving rapid localised gene expression at wound sites (or sites of pathogen invasion) in transgenic plants (van Locht, Meier, Hahlbrock and Somssich (1990): A 125 bp promoter fragment is sufficient for strong elicitor-mediated gene activation in parsley. *The EMBO Journal,* 9: 2925–2950; Lois, Dietrich, Hahlbrock and Schulz (1989) A phenylalanine ammonia-lyase gene from parsley: structure, regulation and identification of elicitor and light responsive cis-acting elements. *The EMBO J.* 8: 1641–1648; Doerner, Stermer, Schmid, Dixon and Lamb (1990) Plant defense gene promoter gene fusions in transgenic plants: tools for identification of novel inducers. *Bio/technology,* 8: 845–848; Rhee, Kan, Gonzalez and Bol (1990). Analysis of regulatory elements involved in the induction of two tobacco genes by salicylate treatment and virus infection. *The Plant Cell* 2: 357–366). Other genes (eg. chitinase) have provided promoters that are induced more slowly and show peak expression levels after 2–3 days (Roby, Broglie, Cressman, Biddle, Chet, and Broglie (1990) Activation of a bean chitinase promoter in transgenic tobacco plants by phytopathogenic fungi. *The Plant Cell,* 2: 999–1007). Many of these promoters are also inducible by chemical 'elicitors'. The data regarding the activity of these promoters have normally been obtained using a 'reporter' gene such as GUS to monitor gene expression.

The above studies on wounding and the isolation of plant 'defence' genes and their promoters have concentrated on dicotyledonous plants. There is little or no evidence that such promoters are active in monocotyledons (eg cereals) and it is widely recognised that this group of plant species have proven to date to be very difficult to engineer genetically, using any technique.

To be useful in plant transformation procedures promoters are required that are rapidly induced at wound sites of both dicotyledons and monocotyledons and expression from such promoters should persist for several days post-wounding in cells which are targets for transformation and on which selection for transformation is imposed. The utility of such promoters would be greatly enhanced if they were also functional in actively dividing, organogenic/embryogenic cultured cells and in other cell types in embryos and organ primordia (identified above in Table 1) that represent targets for transformation by direct DNA transfer techniques.

The properties which render a promoter useful as a component in a selectable manner system as described also render it useful in the production of compounds in plant cell culture.

According to a highly preferred embodiment of the first aspect of the present invention, there is provided a recombinant or isolated DNA molecule comprising a promoter which naturally drives the expression of a gene encoding a predicted 16.92 kDa protein after and/or during wounding and/or callus formation in *Asparagus officinalis* or an equivalent protein in other members of Liliaceae or Amaryllidaceae.

In this specification the gene encoding the 16.92 kDa protein in *Asparagus officinalis* and equivalents of that gene in other members of Liliaceae or Amaryllidaceae will be referred to as the AoPR1 gene. The AoPR1 gene is different in sequence and pattern of expression from other wounding induced or pathogen induced or elicitor induced or callus-specific genes described in the scientific literature. The AoPR1 gene has limited homology to a class of PR1-type proteins found in dicotyledonous plants. Several of these proteins are known to be expressed adjacent to wound sites and in some cases have been shown to be inducible by elicitor treatment. However, the AoPR1 gene described in the present invention differs markedly in its transcription profile from other PR-1 type genes in that it is quickly upregulated and highly active in wounded plant material both in wounded seedlings and in tissue cultured explants and its high expression persists for many days post-wounding at the wound site in explants and in callus cells and suspension cultured cells derived from the original wounded tissue.

AoPR1 gene expression is largely limited to the locality of the wound site in asparagus seedlings and in tissue cultured cells which are the primary sites for transformation by Agrobacterium-based methods and by direct DNA delivery methods. Unlike other wounding-induced promoters that have been described, the AoPR1 gene is expressed in the cell types that may be subjected to selection treatment during a transformation process and additionally the AoPR1 gene can be induced by salicylic acid. Particular attention is drawn to the fact that the majority of the cell types in growing plants do not express the AoPR1 gene; this is an important feature, as any promoter isolated from the AoPR1 gene that is used to drive marker gene expression will ensure only a minimal amount of unwanted marker gene product in transgenic plants.

The molecular weights of the AoPR1 gene product are putative and derived from the number of amino acids believed to be present, as deduced from the DNA sequence. The 16.92 kDa protein encoded by the AoPR1 gene has 158 amino acids. It will therefore be appreciated that the molecular weights refer to the unmodified protein and any effect of post-translational processing, such as partial proteolysis, is discounted.

Although the figure given above relates only to proteins of *Asparagus officinalis* those skilled in the art will readily be able to identify equivalent proteins from other members of the family Liliaceae or the related group Amaryllidaceae. These equivalent genes may be isolated by nucleic acid hybridisation studies, Restriction Fragment Length Polymorphism (RFLP) mapping, PCR cloning and other methods known in the art. Genes or other DNA encoding closely equivalent proteins may for example hybridise under stringent conditions (such as approximately 35° C. to 65° C. in a salt solution of approximately 0.9 molar) to the AoPR1 gene, or fragments of them of, for example, 10, 20, 50 or 100 nucleotides. A 15–20 nucleotide probe would be appropriate under many circumstances. For example, PCR primers designed against the AoPR1 gene sequence may be used to amplify the gene from mRNA from other members of Liliaceae and Amaryllidaceae.

The preferred AoPR1 promoter described in this specification is from *Asparagus officinalis* and can be isolated by methods known in the art for example by (a) synthesising cDNA from mRNA isolated from mechanically-wounded and callusing cells of *Asparagus officinalis*, (b) isolating this cDNA, (c) using this cDNA as a probe to identify regions of the plant genome of *Asparagus officinalis* that encode this gene and (d) identifying the upstream (5') regulatory regions that contain the promoter of this DNA. AoPR1 promoters from other members of Liliaceae and Amaryllidaceae are also included in the scope of this invention.

For the purpose of step (a), viable cells can be isolated by mechanical shearing from a range of plant species including both monocots and dicots. In plants such as *Asparagus officinalis*, mechanically isolated cells can be isolated in very large numbers and when placed in a specific growth medium will undergo cellular dedifferentiation, reactivate cell division and eventually form callus. Asparagus cells are a preferred choice for the isolation of wound site and callusing-specific genes as asparagus is a monocotyledon and yet exhibits many of the wound response phenomena usually associated with dicotyledons (ie. cellular dedifferentiation and induction of cell division). Thus it would be expected that promoters isolated from this species may function well in both dicots and monocots. Cultured mechanically isolated cells exhibit many features of wound surface cells which undergo dedifferentiation and callus formation and the present invention demonstrates that such cell populations represent a very enriched source of gene transcripts specifically induced in wounded and tissue cultured cells. A cDNA library can be made from mRNA extracted from mechanically separated cells at different times following cell isolation. Differential screening of the library and testing of random recombinant clones has shown that a large proportion of cDNA clones in the library are wound-inducible again illustrating the utility of mechanically isolated cells as an enriched source of wound-induced and cell culture specific genes. Detailed analysis of the expression of such genes has shown that several different types of expression profiles may be found in in vitro cultured mechanically isolated asparagus cells and in wounded asparagus explants (see FIG. 1). Particular attention is drawn to the fact that certain genes are rapidly induced after wounding/cell isolation and continue to be strongly expressed for more than 7 days post-wounding. One of these genes is also inducible by treatment of asparagus seedling explants by salicylic acid and is the preferred choice for promoter isolation in the development of new marker genes for transformation.

Particularly preferred promoters are those including sequences upstream of the coding regions shown in FIG. 5 as will subsequently be described in the examples. Those skilled in the art will be able to identify with sufficient precision the promoters driving the coding regions and to isolate and/or recombine DNA containing them.

Promoter containing DNA in accordance with the invention can be used in improved marker genes for use in plant transformation, in a variety of ways as will be discussed below. (The use of the word "gene" in this context should not be taken to imply that only natural genes can be driven by promotes of the invention; rather, any appropriate protein-encoding DNA is included within the term "gene".) In an important aspect of the invention, therefore, there is provided a callus active promoter which is operatively linked to DNA which, when expressed, allows selection of, and/or screening for, transformed plant material, or plant cell culture producing a particular compound.

In this aspect of the invention, the callus-active promoter is not restricted to those which are active in monocotyledonous plants, although such promoters (including, especially, the AoPR1 promoter) are preferred. Other suitable promoters include those of defence-related genes in dicotyledonous plants, including PR2 of parsley, Chs-8 and PAL of bean and PR1 in tobacco. The use of any of these promoters in driving marker genes, does not appear to have been suggested by the literature, presumably because the art has concentrated on the use of strong, constitutive promoters in such circumstances.

In another important aspect of the invention, there is provided a callus-active promoter which is operatively linked to DNA involved in the production of a substance sought to be recovered from plant cell or tissue culture. The substance may be a protein, in which case the driven DNA may code for it (or for a precursor of it). Alternatively, the substance may be another compound, or group of compounds, in whose formation an enzyme is involved: in such a case, the driven DNA may ode for the enzyme. Generally speaking, the substance sought to be recovered will be of commercial interest.

Again, in this aspect of the invention, suitable promoters are not limited to those which are active in monocotyledonous plants, although they are preferred.

Particularly, but not exclusively, for the purpose of cultures of plant cells and tissues, DNA useful in the invention may be super-inducible, so as to give enhanced gene expression. Alternatively or additionally, DNA may be modified by the addition of DNA sequences to give stronger expression.

Since an effective transformation system requires a vector marker genes may be incorporated into Agrobacterium-based vectors and may be incorporated into vectors used in transformation methods using the direct delivery of transforming DNA, for example electroporation, microprojectiles or microinjection, using techniques well known to those skilled in the art. DNA in accordance with the invention and incorporating the AoPR1 promoter can target the strong expression of transformation marker genes in cells competent for transformation and on cell types from which transformants are selected during the plant transformation process. Such DNA can also target the strong expression of cell culture products on dedifferentiated cell types useful for production of compounds in culture vessels. It is possible to target the product for secretion outside the cell by adding a transit peptide sequence of the promoter.

A particular feature of the invention is the strong expression of the promoters in wounded tissue/cells and cultured explants derived from both monocotyledons and dicotyledonous. This is in comparison to the often constitutive promoters normally used to drive marker gene expression which are not very highly expressed in monocotyledon tissue or in tissue cultured cells in general. This feature allows for the improvement of transformation efficiency particularly in tobacco by well known methods and can be extended to include other species (including monocotyledons) by methods which are well known in themselves. It is to be anticipated that the use of these marker genes will speed up the development of efficient transformation techniques in plant species where transformation procedures are relatively inefficient and extend transgenic technology into previously recalcitrant or as yet untested plant species.

Figure 13:
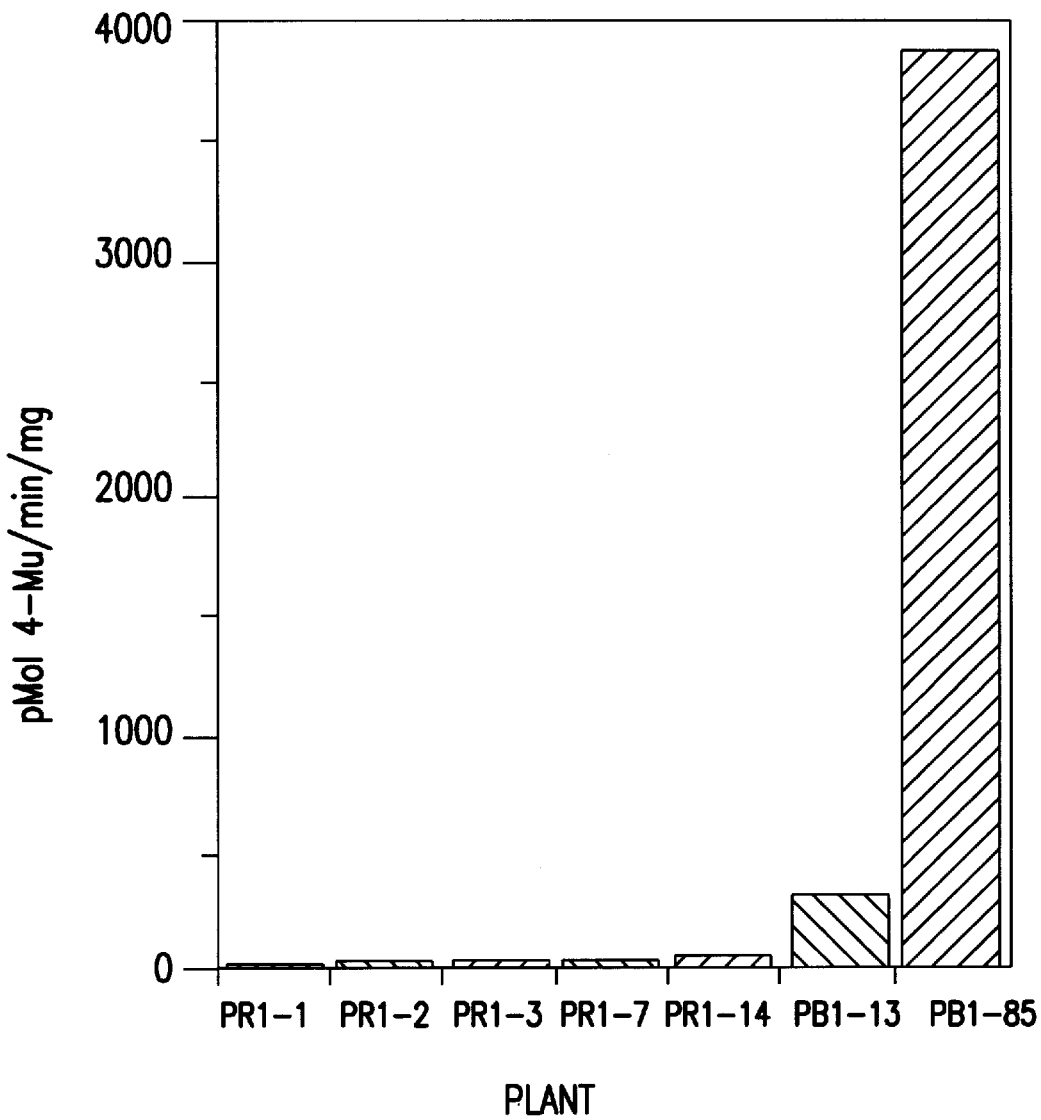
FIG. 13 shows data concerning the expression of the PCR *Asparagus officinalis* AoPR1 GUS gene in mature tobacco leaves as compared to the GUS expression driven by the CaMV35S promoter.

Promoters of the invention are highly wound-site and cell culture/callus specific. The control of expression is very strong and any marker or other gene driven by the AoPR1 promoter shows only very limited expression in the intact transformed plant in planta, apart from its expression at sites of wounding, callusing and pathogen invasion. For example, only a very small amount of expression of the AoPR1 promoter is observed in mature pollen and in the anthacyanin-containing regions of flowers. In relative terms the AoPR1 promoter shows a greater than 1000-fold reduction of marker gene product found in whole harvested transgenic plants (eg. tobacco; FIG. 13) when compared to marker gene product levels in tissue cultured explants. When required to confirm the transgenic nature of a plant, tissue sample can be excised and treated with salicylic acid to induce the AoPR1 promoter, thus allowing marker gene expression to be observed in any tissue type (FIG. 13). It should be noted that this feature is not restricted to the production of marker gene products in transgenic cells and could include the inducible production of any protein in transgenic cells.

An important advantage of the present invention therefore is that the marker gene driven by the AoPR1 promoter will generally not be expressed in the bulk of the cells in the transgenic plant and therefore the majority of the production of unwanted marker gene product is avoided. This feature of the invention will make transgenic plants generated using marker genes driven by the AoPR1 promoter less likely to show any yield depression that may result from expressing constitutively high levels of these unwanted gene products. The amount of AoPR1-driven marker gene product in harvested crop plant is very substantially reduced as compared to plants transformed using conventionally driven marker genes. This feature should substantially lessen any possible real or conceived detrimental environmental impact of transgenic plant release into general agricultural practice and avoid the accumulation of unwanted protein products and/or enzymatic activities in plant-derived foodstuffs. These features should improve the marketability of transgenic seeds and crops and improve the quality of foodstuffs derived from transgenic crop plants.

The invention is not limited by the particular marker gene driven but a number of promoter-drivable marker gene sequences are preferred. For example, the marker gene may encode an antibiotic or a herbicide resistance gene. The antibiotic or herbicide resistance gene product may modify or degrade a particular class of antibiotic or herbicide and therefore nullify their normally toxic effects on plant cells, thus allowing the transformed plant material to grow on selection medium.

Neomycin phosphotransferase (NPT-II) is an example of an enzyme that can afford resistance to several types of aminoglycoside antibiotics such as neomycin, kanamycin and G418. This is a well known general antibiotic resistance gene used in many transformation systems. Phosphinothricin acetyl transferase (bar) affords resistance to the herbicide phosphinothricin (trade name; BASTA or bialophos) and is a marker gene used to good effect in the transformation of many monocotyledonous species.

β-glucuronidase is a an enzyme that has found particular utility as a screenable marker gene although the AoPR1 promoter could easily be adapted to drive the expression of similar marker genes such as chloramphenicol acetyl transferase (CAT) or luciferase.

It should be recognised that many other coding sequences in selection or screenable markers could be driven by the AoPR1 promoter and that the above list is not an exhaustive one.

Figure 11:
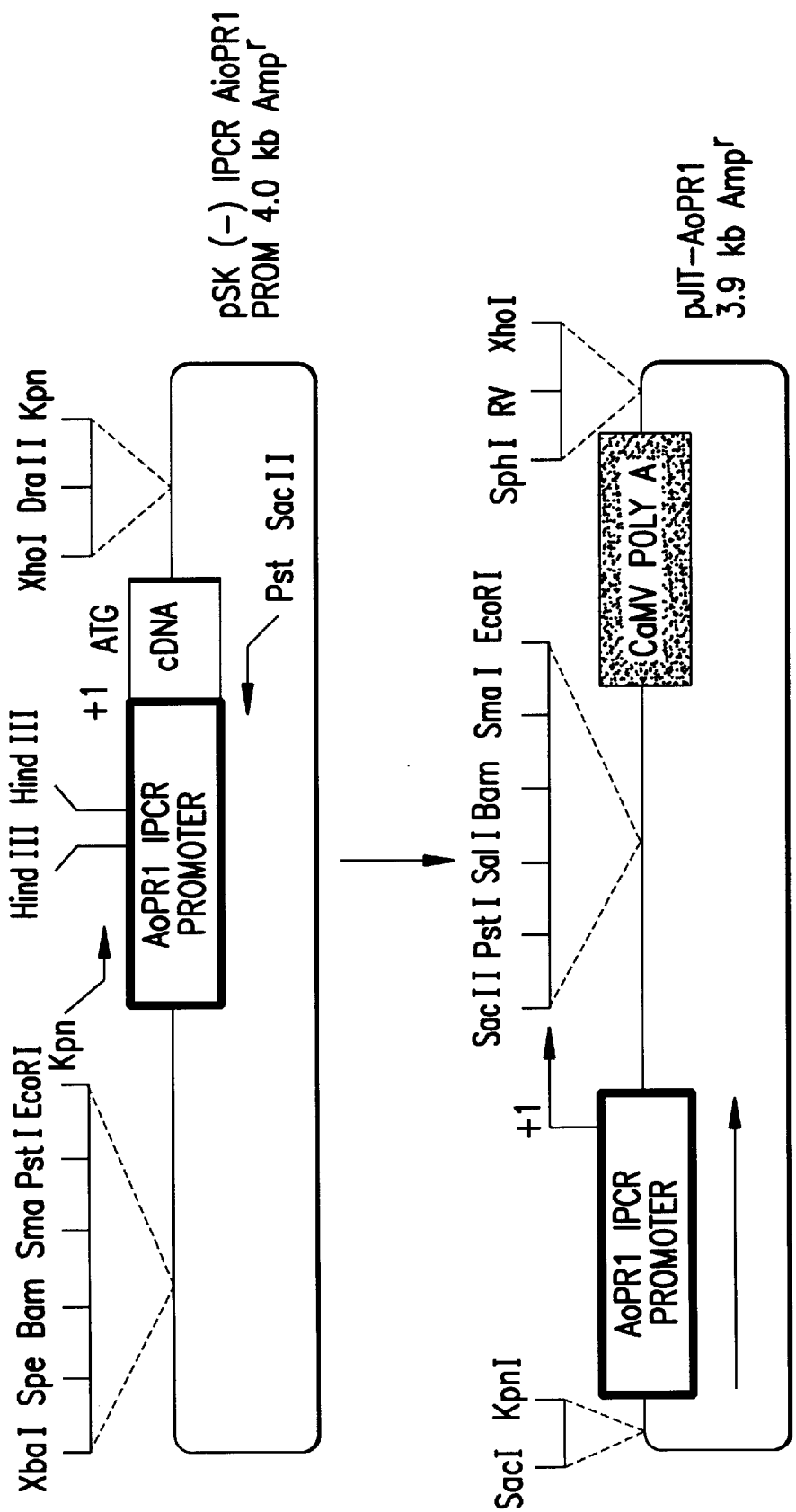
FIG. 11 shows the construction of an expression cassette used to create chimeric genes comprising transcriptional fusions with the *Asparagus officinalis* AoPR1 promoter.

As mentioned above, in an important embodiment of the invention, there is provided DNA encoding a selectable and/or screenable plant marker, the plant marker DNA being operatively coupled to an AoPR1 promoter. In particularly preferred embodiments of DNA sequences of this invention, a 3' transcription regulation signal, such as a polyadenylation signal, may be provided, as may any other regulation sequence. Preferred 3' transcription regulation signals are derived from the Cauliflower Mosaic Virus 35S gene. It should be recognised that other 3' transcription regulation signals could also be used. The AoPR1 promoter may be modified to allow the creation of simple transcriptional gene fusions with the addition of, say, 3' polyadenylation signals from the CaMV 35S gene (FIG. 11).

Recombinant DNA in accordance with the invention may be in the form of a vector. The vector may for example be a plasmid, cosmid or phage. Vectors will frequently include one or more selectable markers to enable the selection of microbial cells transformed (or transfected: the terms are used interchangeably in this specification) with them and, preferably, to enable selection of cells harbouring vectors incorporating heterologous DNA. Appropriate start and stop signals will generally be present. Additionally, if the vector is intended for expression, sufficient regulatory sequences to drive expression will be included; however, DNA in accordance with the invention will primarily be expressed in plant cells, and so microbial host expression would not be among the primary objectives of the invention, although it is not ruled out. Vectors not including regulatory sequences are useful as cloning vectors.

Cloning vectors can be introduced into *E. coli* or any other suitable hosts which facilitate their manipulation. According to another aspect of the invention there is provided a host cell transfected or transformed with DNA described above.

DNA in accordance with the invention can be prepared by any convenient method involving coupling together successive nucleotides, and/or ligating oligo- and/or polynucleotides, including in vitro processes, but recombinant DNA technology forms the method of choice.

Preferably, DNA is transformed into plant cells using a disarmed Ti-plasmid vector and carried by Agrobacterium by procedures which may be known in the art. Alternatively, the foreign DNA could be introduced directly into plant cells using a microprojectile apparatus, or other such physical delivery system. This method is preferred where Agrobacterium is ineffective for stable transformation, for example where the recipient plant is a cereal. Preferably the transformation vector will contain a cloning site or a multicloning site for the insertion of genes or other DNA sequences (these may be referred to as passenger genes in this invention) to be transferred to plant cells. The passenger gene or genes may be under the control of a promoter which has different expression characteristics from the AoPR1 promoter. Any other method that provides for the stable incorporation of the DNA within the nuclear DNA of any plant cell of any species would also be suitable. This includes plant species for which genetic transformation procedures are not yet available.

Ultimately, DNA in accordance with the invention will be introduced into a plant cell by any suitable means. According to a further aspect of the invention, therefore, there is provided a transgenic cell culture (of a monocotyledon or dicotyledon) transformed, for example using microprojectile bombardment or a vector as used in the Agrobacterium transformation technique, with marker DNA operatively linked to an AoPR1 promoter. A whole plant can be regenerated from a single transformed plant cell and the invention therefore provides transgenic plants (or parts of them) including DNA in accordance with the described invention. According to a further aspect of the invention, therefore, there is provided transgenic plants, seeds and propagated shoots containing a plant marker gene driven by an AoPR1 promoter.

In accordance with the invention any suitable gene may be inserted into the cloning sites of such vectors for example using techniques well known to those experienced in the art. Any suitable gene (or genes) may then be transferred to a plant cell using suitable vectors incorporating a marker gene controlled by the AoPR1 promoter. According to a further aspect of the invention, therefore, there is provided a transgenic plant containing a marker gene driven by an AoPR1 promoter. In addition, such plants may contain a selected passenger gene. These plants show minimal expression of the marker gene in the majority of plant tissues and the expected expression of the passenger gene in appropriate cell types.

The invention will now be illustrated by the following examples. The following restriction enzyme and other abbreviations are used:

| DNA | Deoxyribonucleic acid |
|---|---|
| PR | Pathogenesis Related |
| Chs | Chalcone synthase |
| PAL | Phenylalanine ammonia lyase |
| GUS | β-glucuronidase |
| kDa | Kilodalton |
| cDNA | copy DNA |
| mRNA | Messenger Ribonucleic Acid |
| AoPR1 | Asparagus officianalis PR1 gene |
| RFLP | Restriction Fragment Length Polymorphism |
| PCR | Polymerase Chain Reaction |

-continued

| CaMV | Cauliflower Mosaic Virus |
|---|---|
| NPT-II | Neamycin phosphotransferase enzyme |
| npt-II | Neomycin phosphotransferase gene |
| G418 | Gentamycin 418 |
| Bar | BASTA resistance gene (Phosphinothricin acetyl transferase) |
| PAT | Phosphinothricin acetyl transferase |
| pat | Phosphinothricin acetyl transferase gene |
| CAT | Chloramphenicol acetyl transferase |
| ORF | Open reading frame |
| IPCR | Inverse Polymerase Chain Reaction |
| X-Gluc | 5-Bromo-4-chloro-3-indolyl glucuronide |
| Pfus | plaque forming units |
| SDS | Sodium dodecylsulphate |
| bp | base pairs |
| dNTP | dexoynucleotide triphosphate |
| CaMV Poly A | Cauliflower Mosaic Virus poly A signal |
| PROM | Promoter |
| CaMV35S | Cauliflower Mosaic Virus 35S transcript |
| S/D | Shine/Daigarno sequence |
| RV | EcoRV |
| Kpn | KpnI |
| Kan | Kanamycin |
| Amp | Ampicillin |
| Bcl | BclI |
| Bgl | BqlII |
| Acc | AccI |
| H3 | HindIII |
| Xho | XhoI |
| RI | EcoRI |
| Sac | SacI |
| Eco | EcoRI |
| Sma | SmaI |
| Bam | BamHI |
| Pst | PstI |
| Not | NotI |
| Spe | SpeI |
| Dra | DraII |
| Cla | ClaI |
| Sal | SalI |
| Xba | XbaI |
| Nos | Nopaline synthase |
| Poly (A) | Polyadenylation signal sequence |

The examples refer to the accompanying drawings, as described above.

DETAILED DESCRIPTION OF THE FIGURES

Figure 7A:
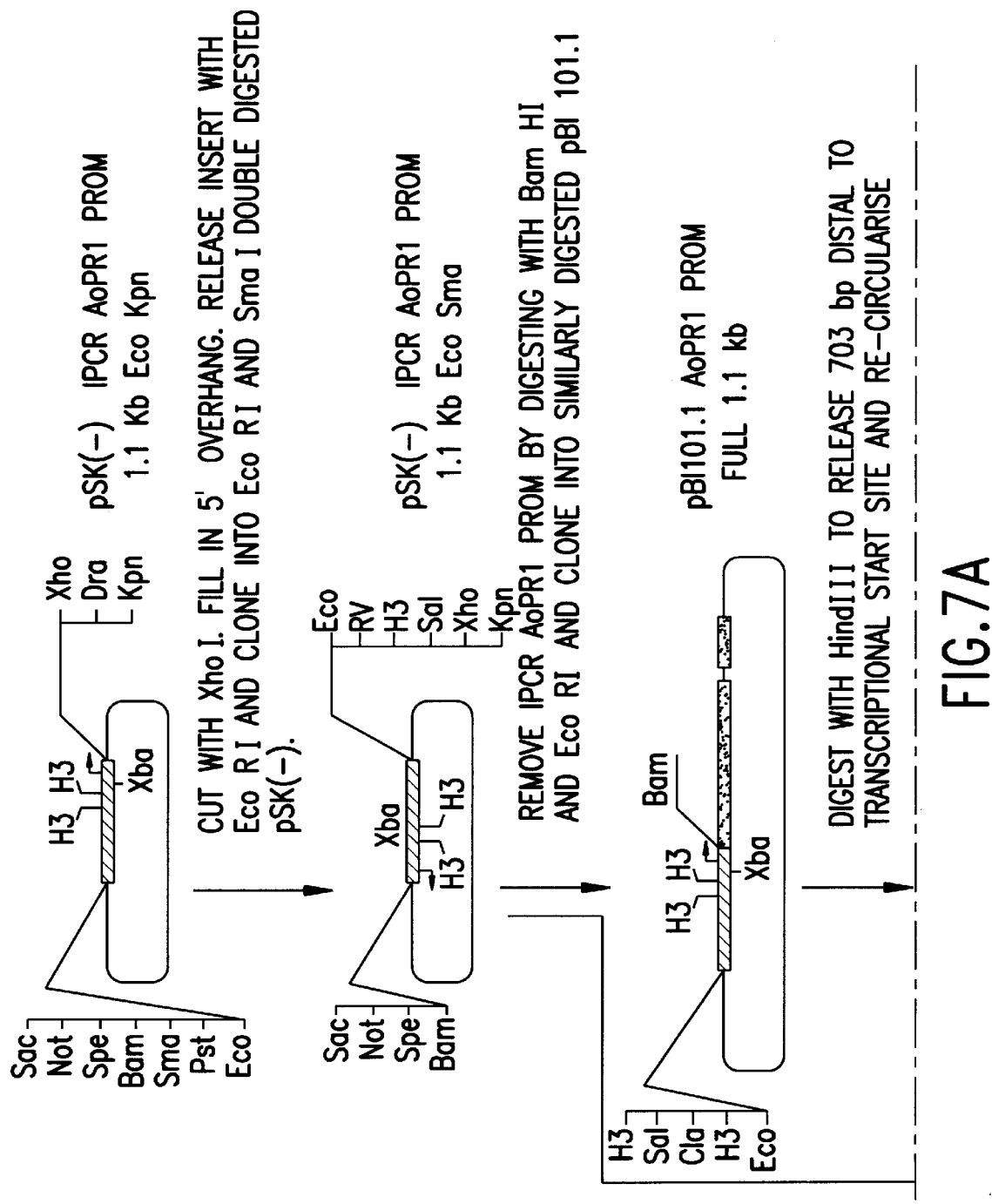
FIG. 7a shows the construction of a chimeric gene containing a translational fusion between the *Asparagus officinalis* AoPR1 promoter and an *E. coli* gene encoding B-glucuronidase (GUS) in an Agrobacterium vector.
Figures 1, 7A:
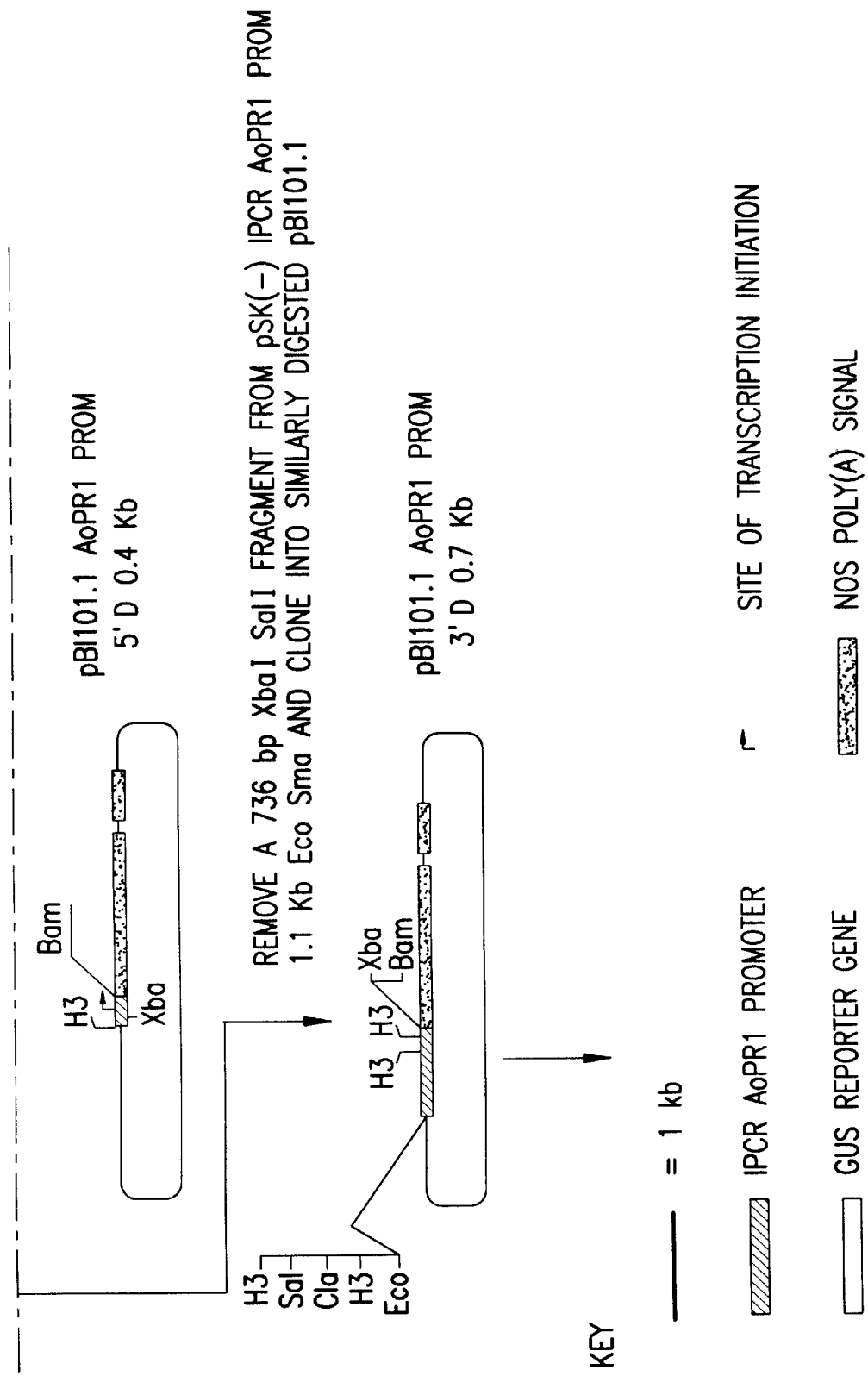
FIG. 1 shows a table of data relating to the frequency of wound-site/callus specific cDNA clones in a library prepared from mRNA purified from mechanically isolated asparagus cells.

FIG. 1 shows a table of data relating to the frequency of wound-site/callus specific cDNA clones in a library prepared from mRNA purified from mechanically isolated asparagus cells. Clone numbers 3 to 39 are random 'cold' clones chosen from cDNA library following prescreen with labelled first strand cladode DNA; clone numbers A5 to A17 are random clones isolated from cDNA library. Comments in relation to various of the clone numbers are as follows:

| 3: | Low abundance, peak day 1–3; |
|---|---|
| 5: | Cells, high abundance peak day 3; Plant, high abundance, peak day 1–3; |
| 22: | Low abundance, peak day 1; |
| 28: | Cells, low abundance, peak day 3–5; Plant, low abundance, peak day 1; |
| 30: | Medium abundance, peak day 3; |
| 34: | Medium abundance, peak day 3; |
| 37: | Medium abundance, constitutive, peaks day 3 in cells and day 1 in plants; |

-continued

| | |
|---|---|
| 39: | Cells, high abundance, peak days 1–3; Plant, medium abundance, peak 3; |
| A11: | Cells, low abundance, peak days 1–3; Plant, low abundance, peak day 1; |
| A12: | Medium abundance, peak day 1; |
| A16: | Medium abundance, present day 1 only. |

Note: 17% of plaques showed a positive signal when screened with cladode first strand cDNA. Approximately 30% of randomly chosen clones are wound-induced or induced by cell culture.

Figure 2B:
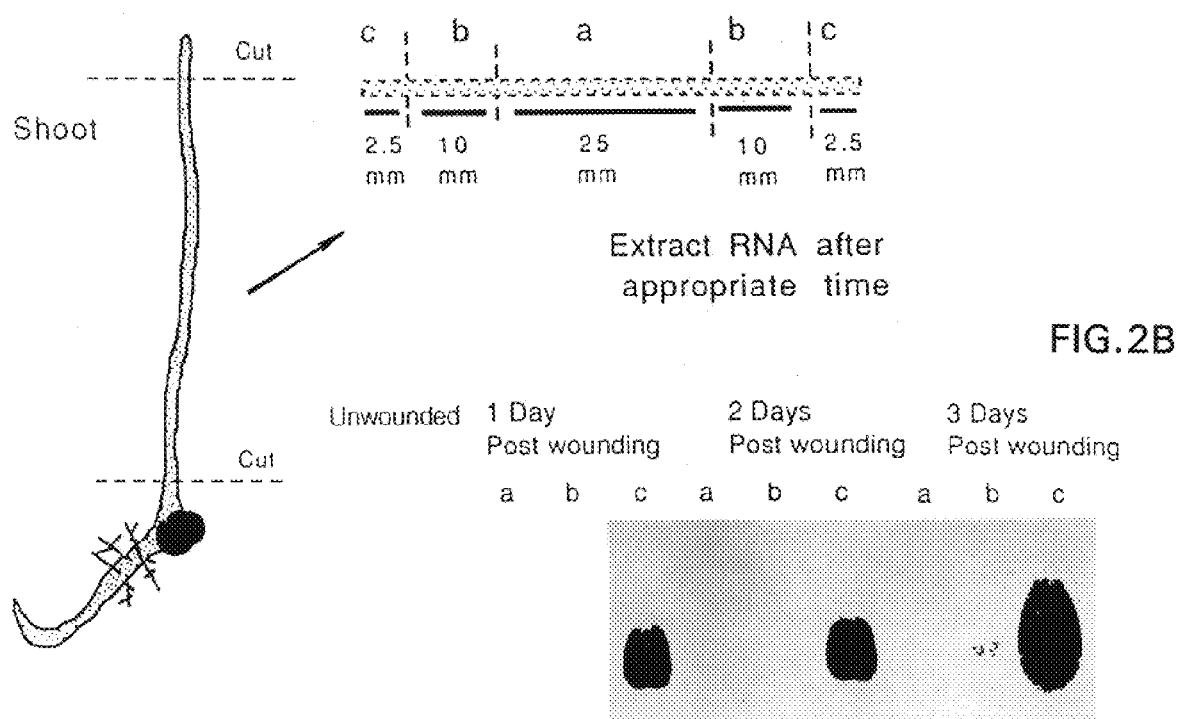
FIG. 2b shows Northern analysis of transcript abundance at wound site.

FIGS. 2a and 2b show RNA hybridisation (northern) experiments illustrating the induction profile of the AoPR1 gene in explants from asparagus tissue.

FIG. 2a shows Northern analysis of transcript following cell isolation and wounding. Total RNAs were extracted from unwounded seedlings (lane 1), cell suspension one day post isolation (lane 2), seedlings cut into 2 mm length sections one day post wounding (lane 3), seedlings cut into 10 mm length sections one day post wounding (lane 4), cell suspension two days post isolation (lane 5), seedlings cut into 2 mm length sections two days post wounding (lane 6), seedlings cut into 10 mm length sections two days post wounding (lane 7), cell suspension three days post isolation (lane 8), seedlings cut into 2 mm length sections three days post wounding (lane 9), seedlings cut into 10 mm length sections three days post wounding (lane 10), run out on denaturing gels, blotted and hybridised with probes made from the AoPR1 cDNA.

FIG. 2b shows Northern analysis of transcript abundance at the wound site. Total RNAs were extracted from unwounded seedlings and from 5 cm wounded mesocotyl explants at 1, 2 and 3 days post wounding: (a), 25 mm length sections 12.5 mm away from the wound site; (b), 1 mm length sections 2.5 mm away from the wound site; (c), 2.5 mm length sections that include the wound site. Total RNA was run out on denaturing gels, blotted and probed with the Wip-1 cDNA.

FIG. 3 shows the DNA sequence of the AoPR1 cDNA (SEQ ID No:5) together with the deduced protein sequence (SEQ ID No:6) of the ORF contained in the *Asparagus officinalis* AoPR1 cDNA. Underlined regions show positions of EXT 1 and IPCR 1 primers used for inverse PCR.

Figure 4:
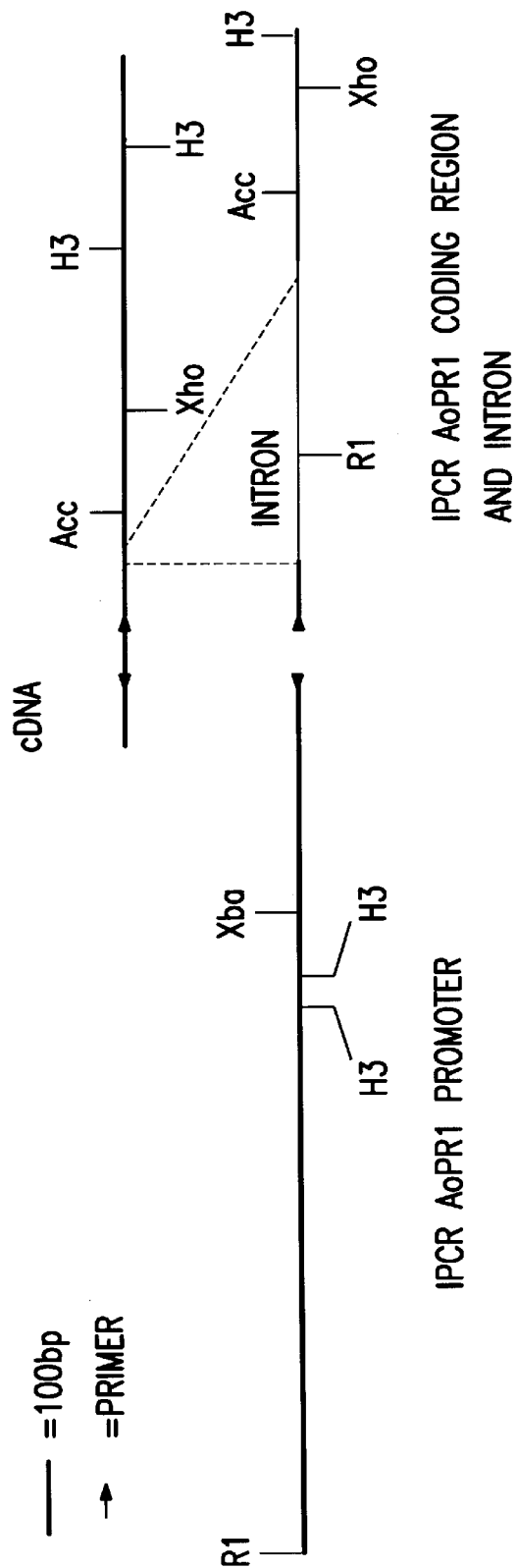
FIG. 4 shows the strategy employed for cloning the *Asparagus officinalis* AoPR1 gene and its upstream regulatory elements.

FIG. 4 shows the strategy employed for cloning the *Asparagus officinalis* AoPR1 gene and its upstream regulatory sequences using an approach based on an inverse polymerase chain reaction (IPCR) technique.

FIG. 5 shows the nucleotide sequence (SEQ ID No:7) of the *Asparagus officinalis* AoPR1 gene promoter generated by IPCR, with predicted coding sequence (SEQ ID No:8). The predicted TATA box is underlined. The transcriptional start site as determined by Nuclease-S1 mapping is shown as a bold underlined character.

FIG. 6 shows an alignment of the *Asparagus officinalis* AoPR1 cDNA and the AoPR1 gene PROM fragment. Percent identity: 98.90%.

FIG. 7a shows the construction of a chimeric gene containing a translational fusion between the *Asparagus officinalis* AoPR1 promoter and an *E. coli* gene encoding β-glucuronidase in an Agrobacterium binary vector.

Figure 7B:
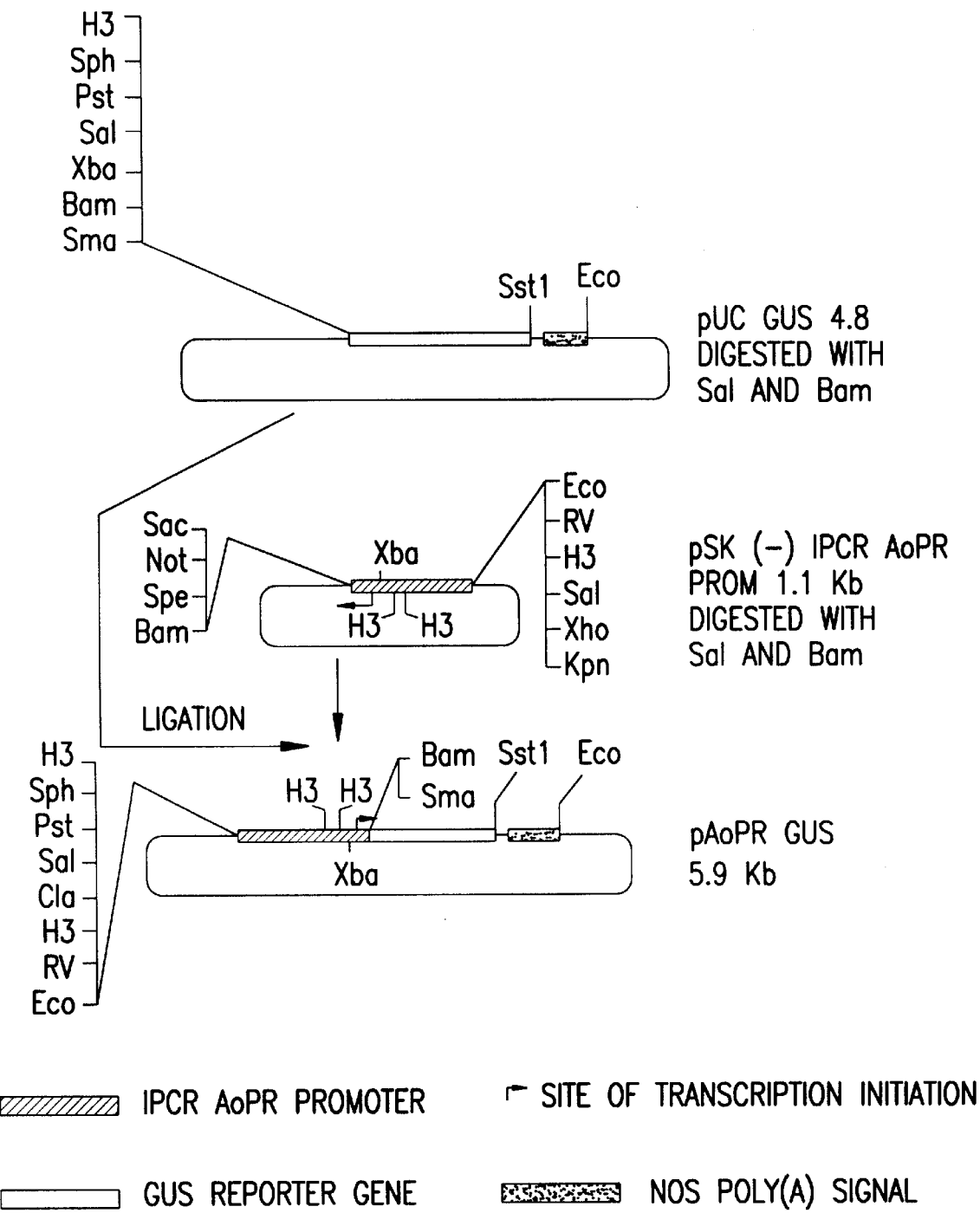
FIG. 7b shows the construction of a chimeric gene containing a translational fusion between the *Asparagus officinalis* AoPR1 promoter and an *E. coli* gene encoding GUS in a small high copy number plasmid suitable for direct gene transformation techniques.

FIG. 7b shows the shows the construction of a chimeric gene containing a translational fusion between the *Asparagus officinalis* AoPR1 promoter and an *E. coli* gene encoding β-glucuronidase (GUS) in a small high copy number plasmid suitable for direct gene transfer transformation techniques.

Figure 8A:
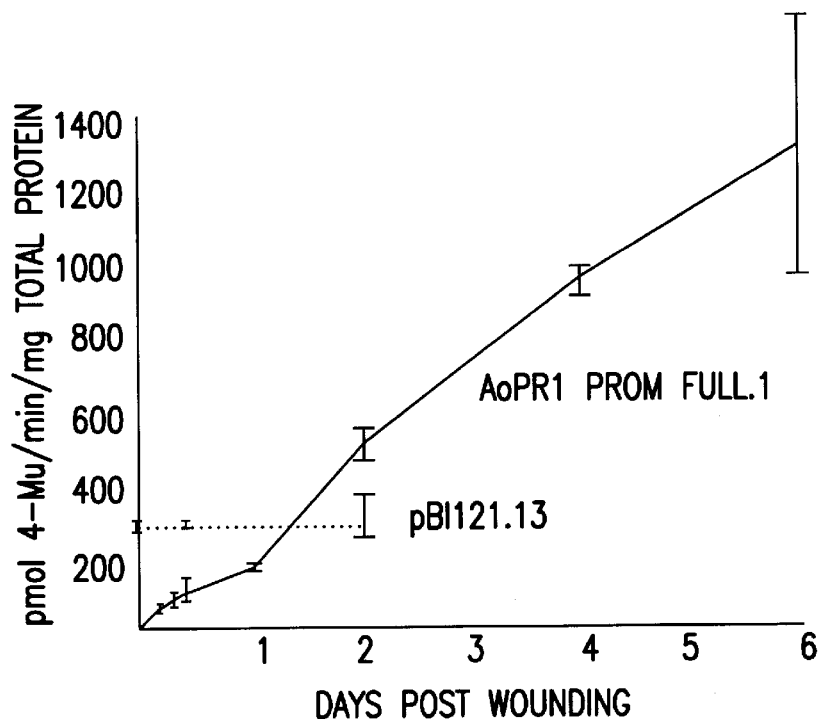
FIG. 8 shows the induction of the chimeric gene containing a translational fusion between the *Asparagus officinalis* AoPR1 promoter and an *E. coli* gene encoding GUS following wounding of transgenic tobacco plant tissue.
Figure 8B:
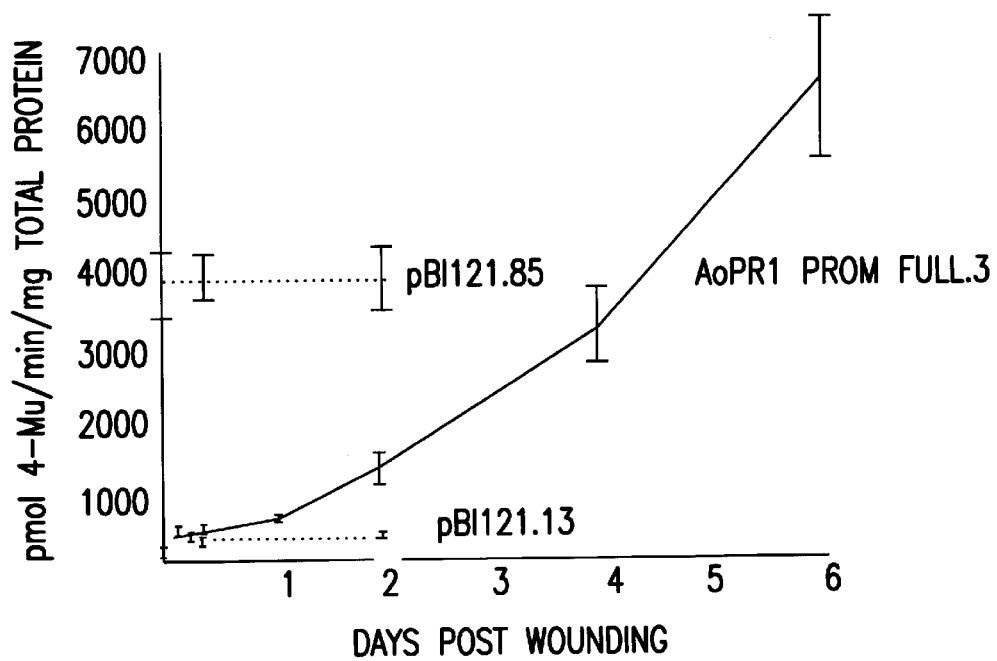
Figure 8C:
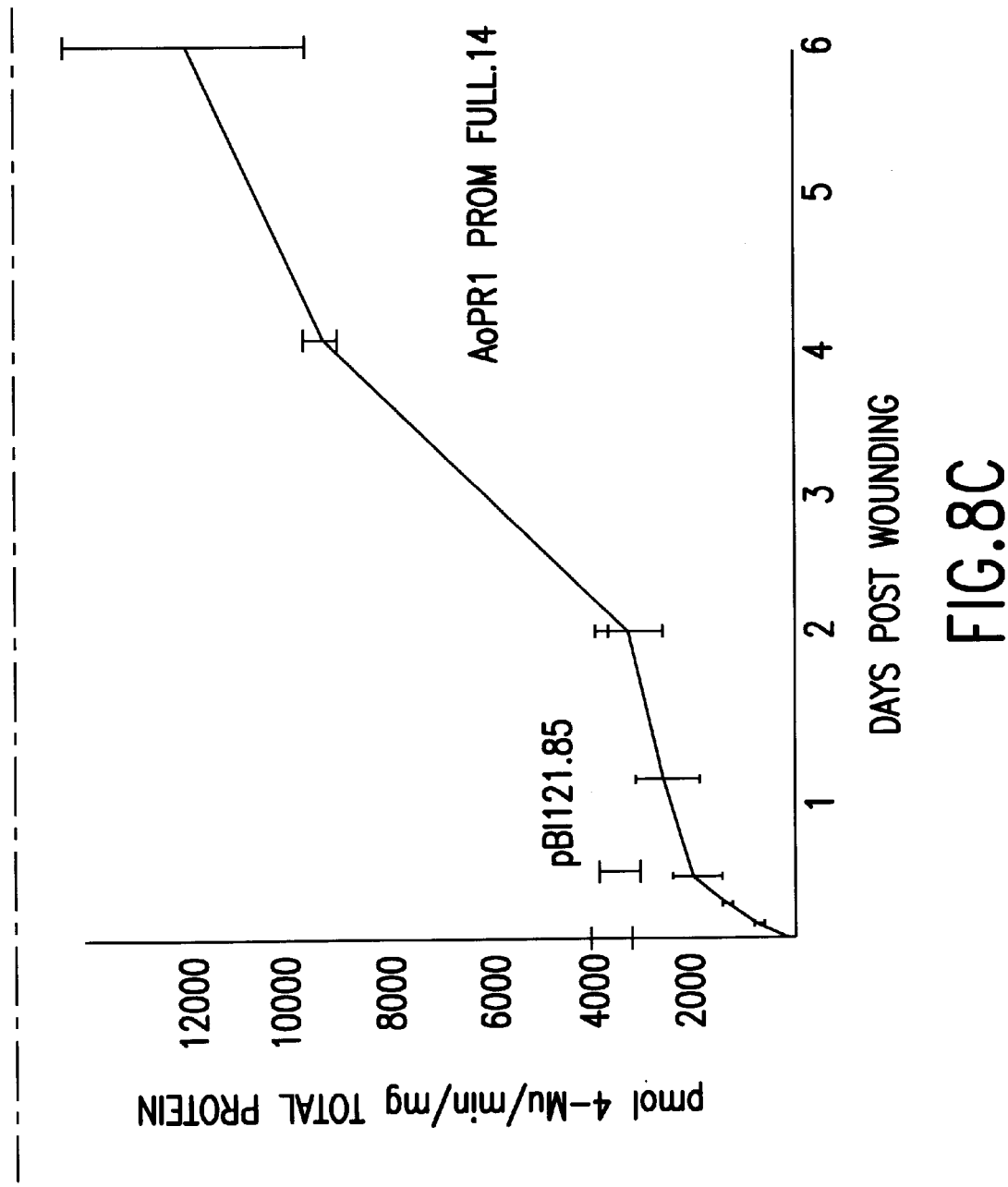

FIG. 8 shows the induction of the chimeric gene containing a translational fusion between the *Asparagus officinalis* AoPR1 promoter (from (a) FULL.1, (b) FULL.3 and (c) FULL.14) and an *E. coli* gene encoding β-glucuronidase following wounding of transgenic tobacco plant tissue.

Figure 9:
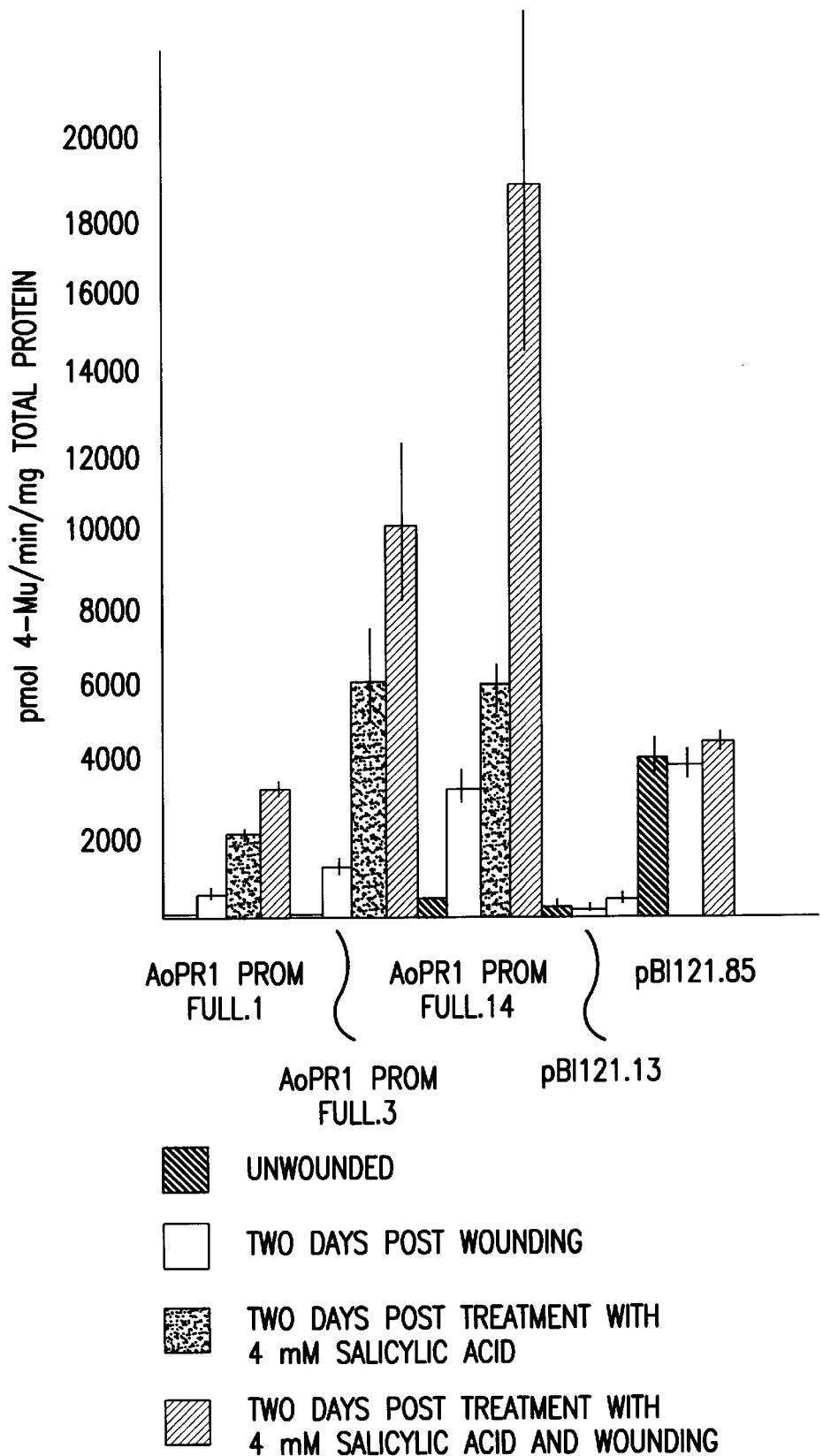
FIG. 9 is a histogram showing data concerning the induction of the chimeric gene containing a translational fusion between that *Asparagus officinalis* AoPR1 promoter and an *E. coli* gene encoding GUS following treatment of plant tissue by 4 mM salicylic acid.

FIG. 9 is a histogram showing data concerning the induction of the chimeric gene containing a translational fusion between the *Asparagus officinalis* AoPR1 promoter and an *E. coli* gene encoding β-glucuronidase following treatment of plant tissue by 4 mM salicylic acid.

Figure 10:
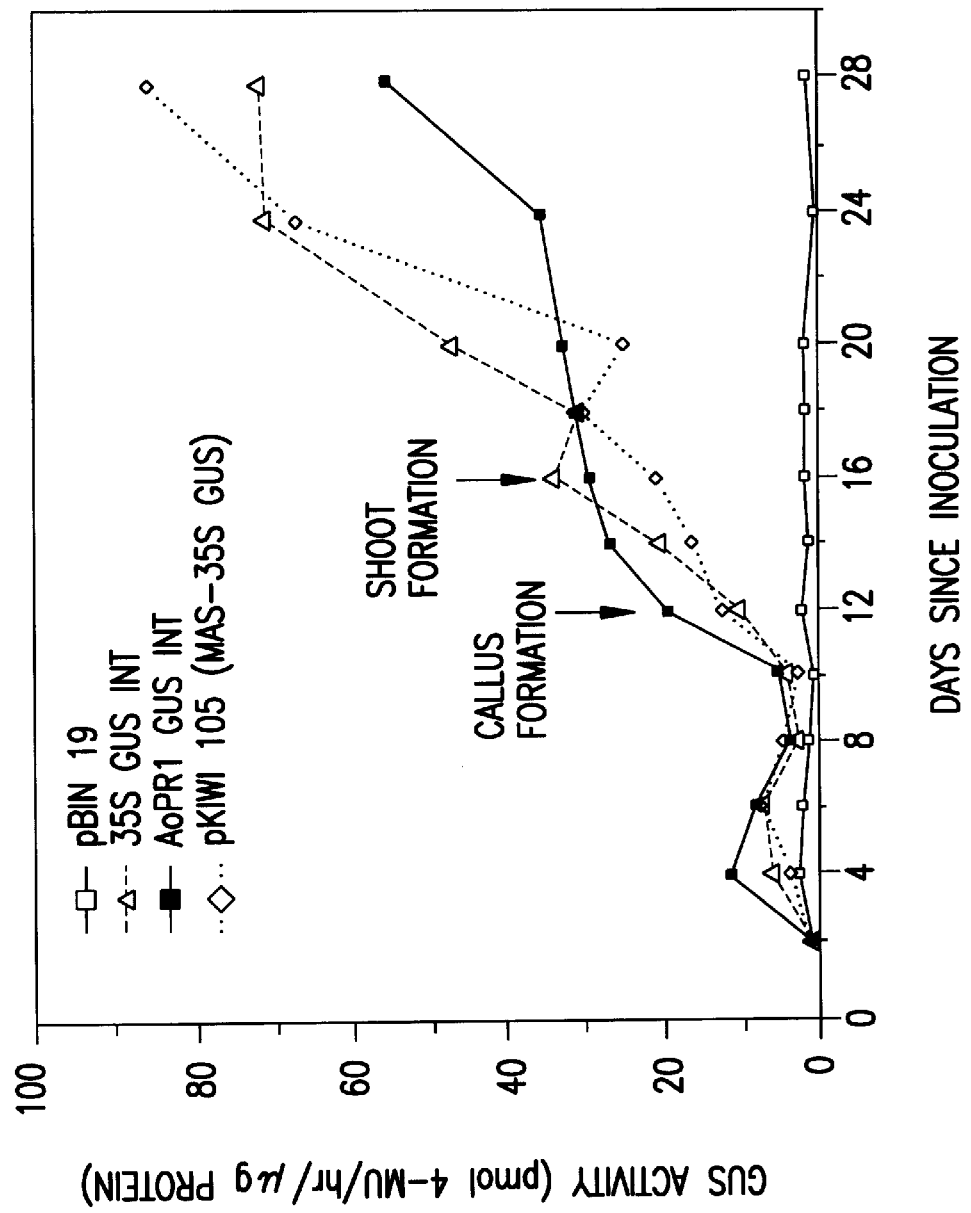
FIG. 10 shows GUS marker gene expression during the transformation of tobacco leaf disc when the gene is driven by different promoters.

FIG. 10 shows GUS marker gene expression during the transformation of tobacco leaf discs when the gene is driven by different promoters. For plasmids see text except for p35S GUS INT which is as described by Vancanneyt et al., (1990) Construction of an intron-containing marker gene, *Molecular and General Genetics* 220, 245–250).

FIG. 11 shows the construction of an expression cassette used to create chimeric genes comprising transcriptional fusions with the *Asparagus officinalis* AoPR1 promoter.

Figure 12A:
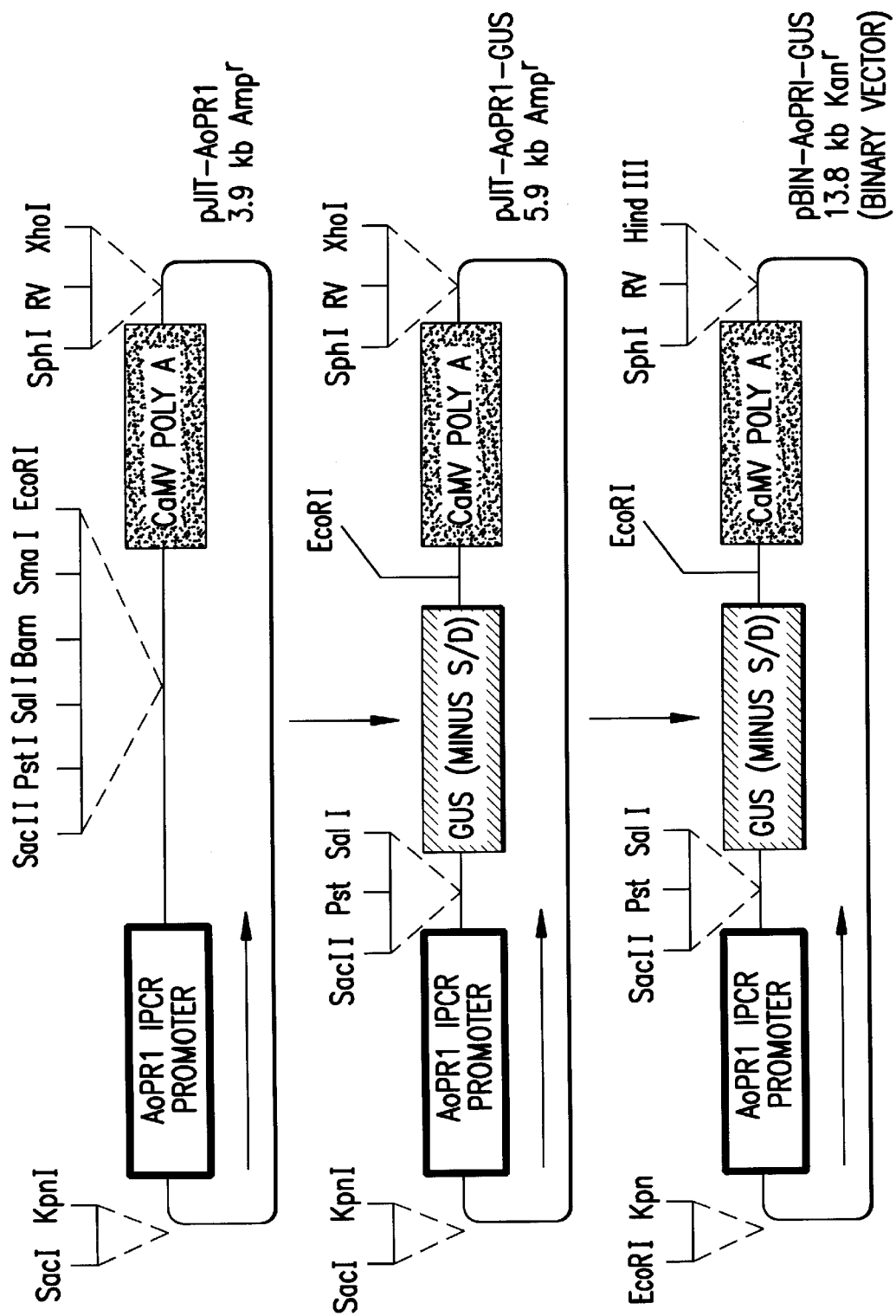
FIG. 12a shows the construction of a transcriptional fusion between the *Asparagus officinalis* AoPR1 promoter and an *E. coli* gene encoding GUS (AoPR1-GUS gene).

FIG. 12A shows the construction of a transcriptional fusion between the *Asparagus officinalis* AoPR1 promoter and an *E. coli* gene encoding β-glucuronidase (AoPR1-GUS gene).

FIG. 12B shows the construction of an AoPR1-GUS-INT transformation vector.

FIG. 13 shows data concerning the expression of the PCR *Asparagus officinalis* AoPR1 GUS gene in mature tobacco leaves as compared to the GUS expression driven by the CaMV35S promoter. PR1—1, PR1-2, PR1-3, PR1-7, and PR1-14 are independent transformants containing the AoPR1 GUS gene whilst pBI-13 and pBI-85 are two examples of plants transformed by pBI121 which contains a GUS gene driven by the CaMV35S promoter.

Figure 14:
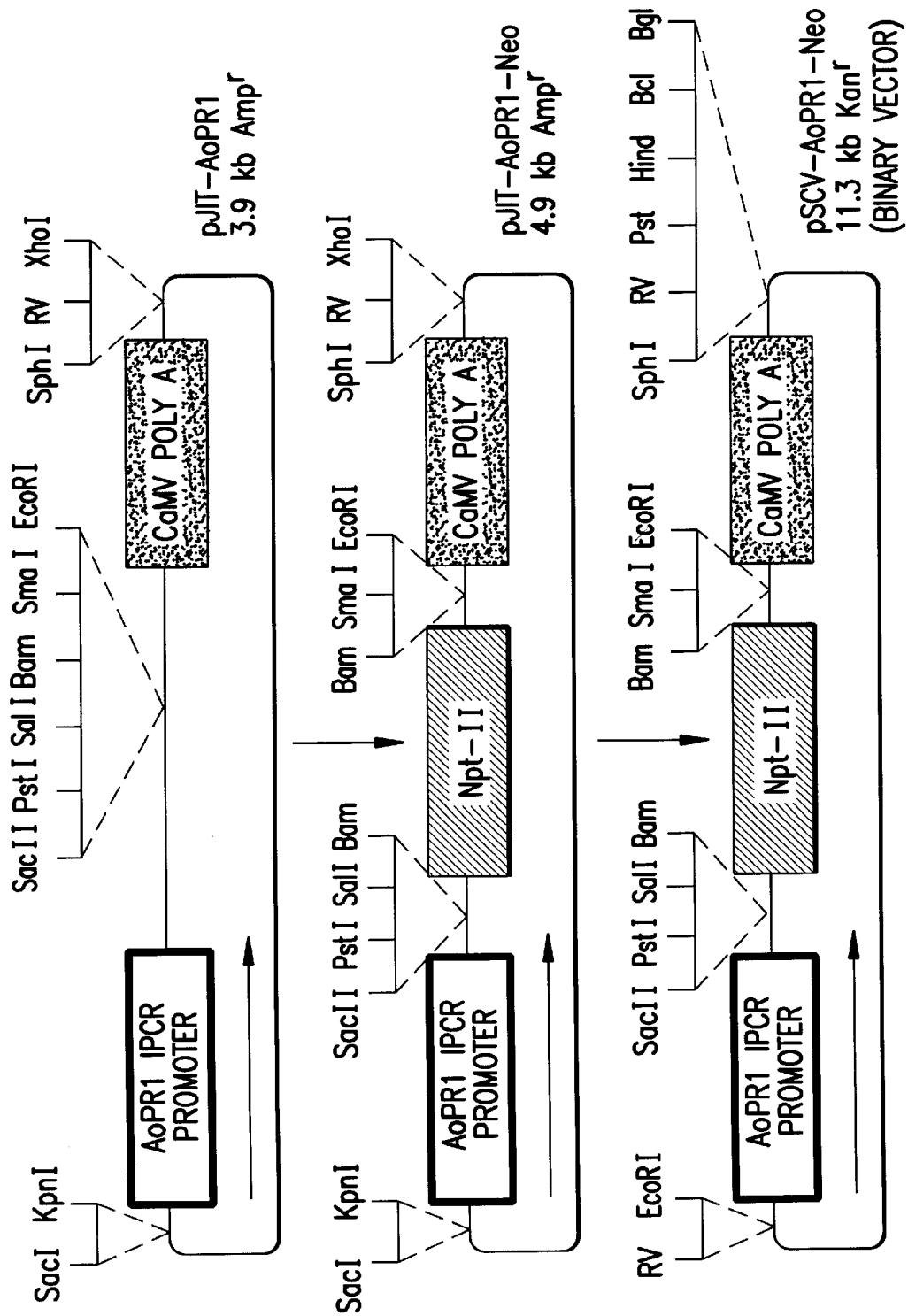
FIG. 14 shows the construction of a transcriptional fusion between the *Asparagus officinalis* AoPR1 promoter and an *E. coli* gene encoding neomycin phosphotransferase derived from transposon 5 (Tn 5).

FIG. 14 shows the construction of a transcriptional fusion between the *Asparagus officinalis* AoPR1 promoter and an *E. coli* gene encoding neomycin phosphotransferase derived from transposon 5 (Tn5).

Figure 15:
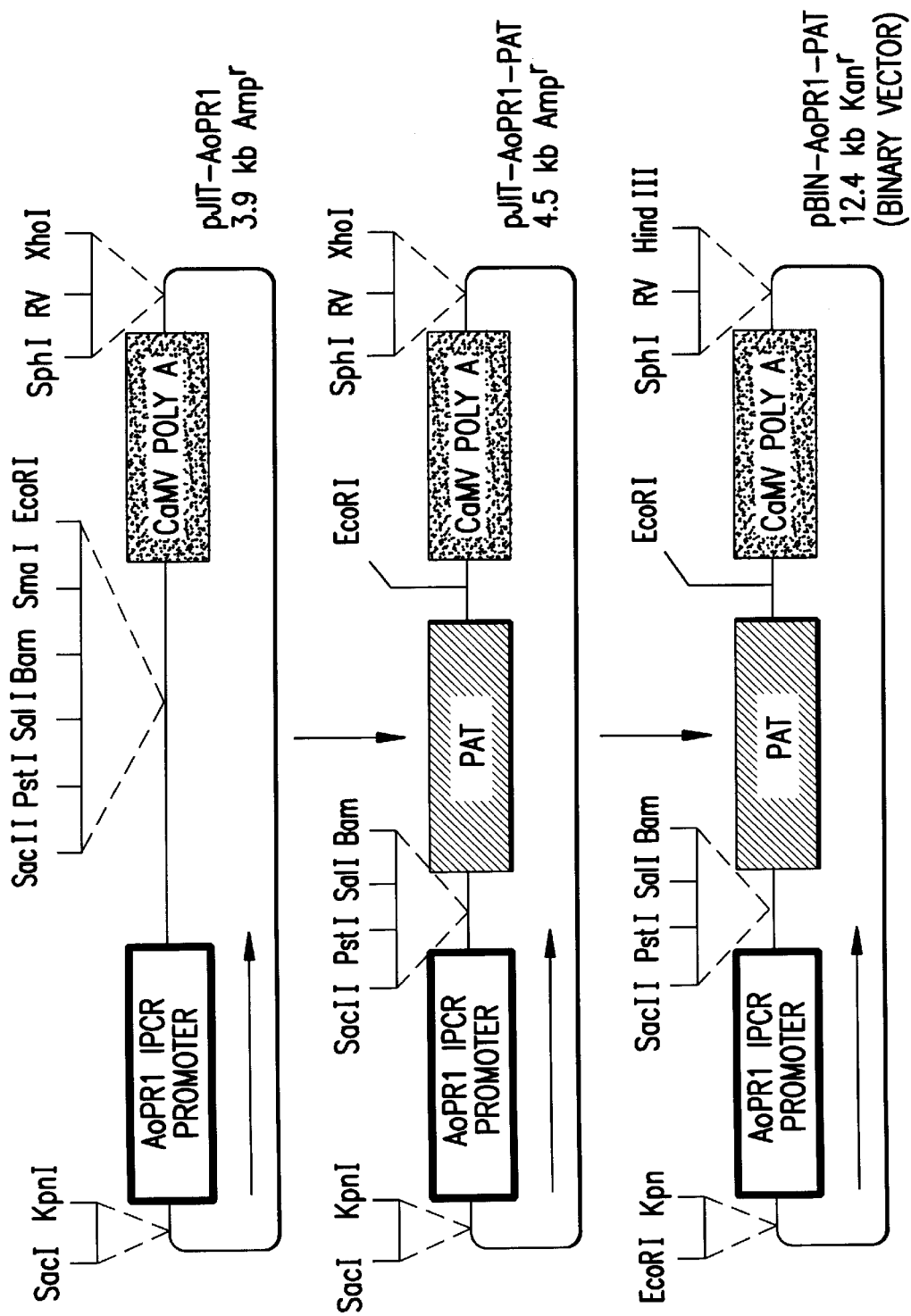
FIG. 15 shows the construction of a transcriptional fusion between the *Asparagus officinalis* AoPR1 promoter and a streptomyces gene encoding phosphothricin acetyl transferase.

FIG. 15 shows the construction of a transcriptional fusion between the *Asparagus officinalis* AoPR1 promoter and a streptomyces gene encoding phosphinothricin acetyl transferase.

EXAMPLES

Example 1

Construction of a library containing an enriched source of cDNAs representative of genes strongly expressed both at wound sites and during callus formation in vitro It has been observed that viable, single cells can be mechanically isolated from *Asparagus officinalis* in large numbers and that such cells are capable of dedifferentiating and initiating cell division given the correct culture medium. There are data which suggest that large changes in gene expression was occurring in these isolated cells [Harikrishna, K., Darby, R. Paul, E. and Draper, J. (1991): Wound response and cell cycle reactivation in mechanically isolated *Asparagus mesophyll* cells: A model monocotyledon system. In press *J. Ex. Bot.*] as they are adapting to the cell culture environment. It is shown here that many genes are indeed upregulated in these mechanically isolated cells and that mRNA isolated from these cells is a very enriched source of genes induced specifically at wound sites in plants and during callus formation.

Materials and methods

Plant growth and cell isolation

*Asparagus officinalis* (c.v. Connover's colossal) seed was purchased from Nickerson Seeds Limited. Greenhouse grown plants were used for cell isolation as described previously [Paul E, Harikrishna K, Fioroni O, Draper J: Dedifferentiation of *Asparagus officinalis* L. mesophyll cells during initiation of cell cultures. *Plant Sci.* 65:111–117 (1989)]. Dark grown seedlings were grown in sterile vermiculite and harvested 2 weeks after germination. The seedlings were then cut into various lengths and incubated on damp filter paper in petri dishes in the dark for the appropriate time.

RNA extractions and poly(A) RNA isolation

Total RNA and poly(A) RNA from isolated cells and wounded seedlings was isolated as described previously [Draper J, Scott R, Armitage P, Walden R: "Plant Genetic Transformation and Gene Expression—A Laboratory Manual" Blackwell Scientific Publications, Oxford (1988)].

Plasmid manipulation and general cloning

Plasmid constructions and manipulations were carried out as described by Sambrook J, Fritsch EF, Maniatis T: "Molecular Cloning—A Laboratory Manual", Second edition, Cold Spring Harbor Laboratory Press (1989). Unless stated otherwise all recombinant DNA procedures and nucleic acid synthesis and analytical methods were carried out using protocols outlined in this manual.

Construction of a cDNA library

2 µg of pooled poly(A) RNA from cultured cells 1–3 days after mechanical separation were used to construct a lambda ZAP-II library. cDNA synthesis was carried out by a modification of the Gubler and Hoffman method [Gubler U, Hoffman BJ: A simple and very efficient method for generating cDNA libraries. *Gene* 25:263–269 (1983)] using a cDNA synthesis kit from Pharmacia. The cDNA was ligated into lambda ZAP II (Stratagene) and the phage packaged using Amersham's packaging extract. The resulting library contained $1.2 \times 10^6$ pfus.

Differential screening of cDNA library to obtain wounding and cell culture-induced cDNA clones 10,000 plaques were plated out at low density (2000 plaques per 15 cm plate) and duplicate HYBOND-N filters were lifted from the plates. (The expression HYBOND-N is a trade mark.) One set of filters was probed with $^{32}$P labelled first strand cDNA synthesised from the same mRNA used to construct the library and the other set probed with $^{32}$P labelled first strand cDNA population synthesised from unwounded seedlings. The labelling, and removal of unincorporated nucleotides was carried out as described [Sambrook J, Fritsch EF, Maniatis T: "Molecular Cloning—A Laboratory Manual", Second edition, Cold Spring Harbor Laboratory Press (1989)]. Hybridisations were carried out essentially as described [Sambrook J, Fritsch EF, Maniatis T: "Molecular Cloning—A Laboratory Manual", Second edition, Cold Spring Harbor Laboratory Press (1989)] in 6×SSPE, 5×Denhardt's solution, 0.5% SDS and 100 µg/ml denatured salmon sperm DNA at 65° C. overnight and the filters washed finally in 0.2×SSC 0.1% SDS at 65° C. Autoradiography was carried out overnight on AMERSHAM β-MAX HYPERFILM. (The expression AMERSHAM β-MAX HYPERFILM is a trade mark.) Differentially hybridising plaques were picked and repurified by another round of differential screening. The clones of interest were then subcloned by automatic excision that follows super-infection of the lambda ZAP-infected host cells with VCS-M13 helper phage according to Stratagene's protocol.

Random screening of cDNA library for wounding and cell culture induced cDNA clones 1,000 plaques were plated out at low density (200 plaques per 15 cm plate) and random recombinant plaques were cored from the library and the cDNA inserts amplified from the lambda Zap vector using PCR primers designed to flank the cloning site in Lambda Zap II and radiolabelled with $^{32}$P using the oligopolist procedure. The labelled cDNA probes were hybridised (northern blotted) against mRNA isolated from cultured asparagus cells (1–3 days post isolation), chopped and aged (2 cm) seedling sections of asparagus and fresh cladode material from asparagus. Northern blots were carried out essentially as described previously [Draper J, Scott R, Armitage P, Walden R: "Plant Genetic Transformation and Gene Expression—A Laboratory Manual", Blackwell Scientific Publications, Oxford (1988)]. Total RNA was run on formaldehyde RNA denaturing gels. The gels were stained in ethidium bromide and blotted. Pre-hybridisation and hybridisation were carried in the same hybridisation solution as for the plaque lifts except the solution contained 50% de-ionised formamide. Clones which hybridised to wounded seedling and cultured cell mRNA but not to cladode mRNA were identified.

Mechanically isolated cells are a rich source of wounding-induced and cell culture-induced genes The library constructed in lambda ZAP-II from message derived from mechanically separated asparagus cells 1–3 days post isolation contained $1.2 \times 10^6$ pfus. Random screening of this library showed that a large proportion of cDNA clones were upregulated in wounded tissues and/or in cells undergoing callus formation (FIG. 1). Highly expressed, wound-induced genes have also been isolated by differential screening of this *Asparagus officinalis* cDNA library.

These data show clearly that mechanically isolated cells are a very enriched source of wound-inducible and cell culture specific mRNA.

Example 2

The isolation and characterisation of the Asparagus cAoPR1 1 cDNA

One particular differentially expressed cDNA clone (named AoPR1) was found to represent up to 1.5% of the cDNA library and was characterised further to evaluate its potential as a source of a gene promoter that would be active at wound sites in explants and active during the callus formation process in cultured plant material.

Additional Materials and Methods

Unless stated the materials and methods used were as indicated in Example 1.

DNA sequencing

The dideoxy chain-termination method [Sanger F, Nicklen S, Coulson AR: DNA sequencing with chain terminating inhibitors. *Proc. Natl. Acad. Sci. USA* 74:5463–5467 (1977)] was used to sequence DNA from the recombinant pSK(-) clones using the SEQUENASE Version 2.0 kit (USB). (The word SEQUENASE is a trade mark.) Single stranded template was prepared by phagemid rescue or by denaturing plasmid DNA as recommended by the USB SEQUENASE booklet. Computer aided sequence analysis and sequence database searches were carried out using the University of Wisconsin released programmes on a VAX [Devereux J, Haeberli P, Smithies O: A comprehensive set of sequence analysis programs for the VAX. *Nucl. Acid Res.* 12:387–395 (1983)].

a) Isolation of the AoPR1 cDNA and characterisation of expression profile

The cAoPR1 1 cDNA was isolated following differential screening of the cDNA library. Northern hybridisation analysis using RNA isolated from mechanically isolated asparagus cells and chopped up seedlings indicate that the corresponding transcript is upregulated both rapidly and persistently following the initial cell isolation event (FIG.

2a). The AoPR1 transcript was detectable from six hours to several days post cell damage in dark grown asparagus seedlings (FIG. 2b). Northern analysis also presented evidence that expression of the AoPR1 gene is regulated in a spatial manner with induction of transcript only being detectable at sites immediately adjacent to the wound site (FIG. 2b). The AoPR1 cDNA could be used to locate homologous genes by Southern hybridisation in DNA prepared from other species of asparagus (eg *Asparagus sperengei*) and other members of Lilliaceae (eg. *Ruscus aculeatus* 'Butchers Broom' and *Muscari neglectum* 'Grape Hyacinth') and Amaryllidaceae. The AoPR1 gene could be isolated by PCR using primers designed against the AoPR1 gene sequence. Northern blot analysis also showed that the AoPR1 gene is expressed in other species of asparagus (eg *Asparagus sperengei*) and related members of Lilliaceae (eg. *Ruscus aculeatus* 'Butchers Broom' and *Muscari neglectum* 'Grape Hyacinth') and Amaryllidaceae.

These data confirmed that the AoPR1—1 gene was an ideal candidate as a source of a wound-site and cell culture inducible promoter and so the cDNA was characterised in detail. In addition it was shown by northern hybridisation analysis that the AoPR1 gene was induced 6-fold in seedlings by salicylate treatment.

b) Sequence of the cAoPR1 1 cDNA

The AoPR1 cDNA is 737 bp in length and contains an open-reading frame (ORF) from position 1 to 475 (FIG. 3). This suggests that this cDNA is not full length. From analysis of the promoter fragment described later the sequence analysis implies that the AoPR1 clone contains all the coding sequence of the gene but does not contain any sequence corresponding to the 5' untranslated region of the transcript. The predicted 16.9 Kda protein encoded by the cDNA has limited homology at the sequence level to members of a protein family as described previously [Walter MH, Jian-Wei L, Grand C, Lamb CJ, Hess D: Bean pathogenesis-related (PR) proteins deduced from elicitor-induced transcripts are members of a ubiquitous new class of conserved PR proteins including pollen allergens. *Mol. Gen. Genet.* 222:353–360 (1990)]. This similarity is yet further evidence that the AoPR1 cDNA is a good target for a gene induced by wounding and explained the observation that it should also be induced by treatment with elicitors such as salicylic acid.

Example 3

The Isolation of the up-stream promoter regions of the AoPR1 gene by the Inverse Polymerase Chain Reaction (IPCR) and the analysis of this DNA Southern blotting analysis revealed a large number of asparagus genomic sequences hybridising with the AoPR1 clone and the screening of an asparagus genomic DNA library lead only to the isolation of genomic clones that did not contain the correct AoPR1 transcript coding DNA sequences. This technique was therefore abandoned as a method to isolate and clone the promoter driving transcription of the AoPR1 gene and instead the AoPR1 gene was isolated by a method known as the Inverse Polymerase Chain Reaction (IPCR).

Additional Materials and Methods

PCR amplification

For Inverse PCR, 1 µg of genomic DNA was digested with an appropriate restriction enzyme. The DNA then phenol chloroform extracted, ethanol precipitated and then resuspended to a concentration of 1–2 ng/µl in 1×ligation buffer (50 mM Tris-Cl pH 7.4, 10 mM $MgCl_2$, 10 mM dithiothreitol and 1 mM ATP) and T4 DNA ligase added to 0.02 Weiss units/µl and allowed to circularise at 15° C. overnight. The DNA was then ethanol-precipitated, dried and resuspended in 20 µl double distilled water and a fifth of this used in the PCR. The reactions were made up as follows:

4 µl of circularised DNA
5 µl of 10×PCR buffer
5 µl of 10×dNTP stock
5 µl of 10×Primer 1 (2.5 µM)
5 µl of 10×Primer 2 (2.5 µM)
double distilled water to give a final volume of 50 µl
2.5 units Taq DNA polymerase.

The reaction mix was then over layed with a few drops of mineral oil and amplified using a Perkin-Elmer Cetus Thermocycler. Thirty cycles of denaturation at 95° C. for 30 seconds, primer annealing at 55° C. for 30 seconds, extension at 72° C. for 3 minutes were performed with a final extension at 72° C. for 5 minutes. The mineral oil was then extracted with chloroform and an aliquot of the PCR products analysed on an agarose gel.

For standard PCR reactions the above PCR protocol was followed with minor adjustments to the number of cycles and annealing temperature.

a) IPCR strategy

Following sequence analysis of the AoPR1 DNA two synthetic oligonucleotide primers of 20 bp were designed such that when used in the inverse polymerase chain reaction technique the resultant amplified DNA would contain upstream sequence from these primers (FIG. 3). The EXT.1 primer which hybridises to the sense strand of the cDNA between the positions 71 to 91 as shown in FIG. 3 reads 5' CGAGGTTGTGCCAGTCGAGC 3' (SEQ ID No:1)

and the IPCR 1 primer which hybridises to the antisense strand of the cDNA between positions 104 to 124 in FIG. 3 reads 5' GCCTGACTTTATTGCCGGTG 3' (SEQ ID No:2).

b) IPCR fragments of AoPR1 gene

IPCR products were obtained in preliminary experiments when the restriction enzymes EcoRI and HindIII were used to digest the asparagus genomic DNA. These products were cloned into pBluscript and used in the construction of a gene map as shown in FIG. 4. The restriction enzyme EcoRI proved useful in the inverse PCR technique allowing the amplification of a 1.3 kb DNA fragment that hybridised with the most 5' region of the AoPR1 cDNA. This PCR product was obtained in sufficient quantities to allow restriction with the EcoRI restriction enzyme and cloning of a 1146 bp fragment into pSK(-) plasmid digested by EcoRI and HincII. The resulting plasmid, named pSK(-)IPCR AoPR1 PROM 1.1 kb Eco RI Kpn, (see FIG. 7a) was digested with XhoI and the resulting single stranded overhangs filled in using the Klenow fragment of DNA polymerase I. The insert was then released from the vector following digestion with EcoRI and ligated into pSK(-) that had been digested with EcoRI and SmaI. The resulting fragment was named pSK(-) IPCR AoPR1 PROM 1.1 kb Eco Sma (see FIG. 7a). DNA sequence analysis of the PCR product confirmed the authenticity of the fragment as the correct up-stream sequences and allowed the correct open reading frame to be determined for translational fusions to be constructed (FIGS. 5 and 6).

c) Determination of transcription start site

To identify the initiation of transcription site on the IPCR AoPR1 promoter the technique of Nuclease-S1 transcript mapping was employed as described previously [Sambrook J, Fritsch EF, Maniatis T: "Molecular Cloning A Laboratory Manual", Second edition, Cold Spring Harbor Laboratory press (1989)]. Using the 1180 bp IPCR AoPR1 PROM purified DNA fragment a probe was prepared from a 846 bp TaqI fragment which was end-labelled following a T4 poly-nucleotide kinase reaction. This was then cleaved with XbaI, generating a 403 bp probe with only the anti-sense strand end labelled at the 5' end. This probe was hybridised to RNA from wounded asparagus cells and subsequently digested with nuclease-S1. The products were run on a sequencing gel alongside a DNA sequence ladder of the same DNA to provide a means of determining the size of the protected fragments. A protected fragment of 132 bp was observed. This indicates that transcription initiates of the AoPR1 transcript occurred at nucleotide 983 (indicated by an underlined bold character in FIG. 5). This knowledge was used in the construction of transcriptional reporter gene fusions in later examples.

Example 4

The construction of GUS reporter translational fusions, demonstrating the ability of the AoPR1 promoter to drive expression of foreign proteins in transgenic plants a) Construction of translational fusions between the AoPR1 promoter and the GUS markers gene Translational fusions of the IPCR AoPR1 promoter (IPCR AoPR1 PROM) were made to the *E. coli* β-glucuronidase (GUS) gene such that: (i) the first 30 amino acids of the fusion protein were encoded by the AoPR1 gene, (ii) the next 11 amino acid were encoded by polylinker DNA and (iii) the rest of the protein derived from the GUS open reading frame (FIG. 7*a*). This was achieved by subcloning the IPCR AoPR1 PROM fragment from pSK(-) IPCR AoPR1 PROM 1.1 kb Eco Sma using a BamHI/SalI, double digest and cloning this 1180 bp fragment into the pBI101.1 binary vector [Jefferson et al., *EMBO J.*, 6:3901 (1987)] that had also been digested with BamHI and SalI. The resultant plasmid formed being described as pBI101.1 AoPR1 PROM FULL1.1 kb. This plasmid was then digested with HindIII and recircularised, releasing a 703 bp fragment distal to the transcriptional start site. This plasmid was named pBI101.1 AoPR1 PROM 5'D 0.4 kb. An XbaI/EcoRI 710 bp fragment from pSK(-)IPCR AoPR1 PROM 1.1 kb Eco Sma cloned into XbaI/EcoRI-digested pBI101.1 resulted in pBI101.1 AoPR1 PROM 3'D 0.7 kb. This construct had the proximal part of the promoter, including the transcriptional start site deleted and was expected to give no GUS activity (FIG. 7*a*).

b) Expression of the GUS marker gene driven by the AoPR1 promoter in transgenic tobacco plants The pBI101.1 AoPR1 PROM constructs were transformed into *Nicotiana tabacum* using standard Agrobacterium transformation techniques as described previously [Draper J, Scott R, Armitage P, Walden R: "Plant Genetic Transformation and Gene Expression—A laboratory Manual, Blackwell Scientific Publications, Oxford (1988)]. The expression of the GUS gene driven by the IPCR AoPR1 promoter constructs were monitored used assays described previously [Draper J, et al., supra]. Histochemical analysis of several transformed plants demonstrate that the 1.1 kb IPCR AoPR1 PROM (IPCR AoPR1) is sufficient to drive the expression of the GUS reporter enzyme in transgenic tobacco at and around the wound sites. This is in contrast to the constitutive CaMV35S promoter which is commonly used to drive expression of marker genes and gives strong expression in all plant tissues. Expression is also observed in mature pollen grains and in the pigmented regions of flowers. The 5'D promoter is unable to drive wound-induced expression of the reporter but is sufficient to drive expression in mature pollen grains. There is no detectable expression of the reporter observed in the transgenic plants carrying the 3'D promoter.

c) Expression of the GUS marker gene driven by the AoPR1 promoter following transformation of cell suspension lines The 1.1 kb IPCR AoPR1 PROM can be released from pBI101.1 by digestion with BamHI and SalI and cloned into the high copy number vector pUC-based vector (pUC GUS 4.8) to create a translational fusion with a GUS gene. (FIG. 7*b*). This small plasmid (pAoPR GUS 5.9 kb) can be prepared in large amounts and used in direct gene transfer transformation techniques such as those utilising microprojectile technology as described by Klein, T., Kornstein, L., Sanford, J. C. and Fromm, M. E. (1989) Genetic transformation of maize cells by particle bombardment. *Plant Physiol.* 91: 440–444.

The 1.1 kb IPCR AoPR1 PROM drives strong expression of the GUS marker gene following transformation of a tobacco cell suspension line using a microprojectile apparatus as described by Klein, et al., supra. Similar results can be obtained with cell suspensions from other dicotyledons (carrot, tobacco, pea) and monocotyledons (asparagus), including cereals (maize & Lollium).

The above data indicate: (a) that the 1.1 kb region of the AoPR1 gene promoter ('FULL Promoter') is sufficient to drive strong of marker genes at wound sites in damaged plant tissue and thus is ideally suited to drive marker genes in Agrobacterium-based plant transformation systems; (b) the AoPR1 promoter has very limited developmental expression (eg, mature pollen and pigmented regions in flowers, parenchyma ray in secondary xylem in woody tissue, seed coat (transiently)) and thus marker gene expression is minimised in seedlings and mature plant tissue; (c) the AoPR1 promoter is stably expressed in suspension cultured cells and is therefore ideally suited to drive expression of marker genes in transformation vectors used in direct DNA delivery techniques.

Example 5

The IPCR AoPR1 promoter is rapidly induced at wound sites and its expression lasts for several days and is equivalent to or greater in strength to the CaMV35S promoter Leaf disks of 1 cm in diameter were isolated from three plants carrying the FULL 1.1 kb IPCR AoPR1 promoter fusion with GUS. These disks were stabbed randomly eight times with a 20 gauge needle and then left to age for several days on damp filter paper in the dark at 25° C. At daily intervals, GUS enzyme activity was assayed fluorometrically. Example expression profiles in wounded leaf disks from three plants carrying the full 1.1 kb IPCR AoPR1 promoter fusions with GUS are shown in FIG. 8. The pattern of expression mirrored that seen in chopped up asparagus seedlings with up-regulation of enzyme activity being observable rapidly and persistently following wounding. Two transformed plants containing the constitutive CaMV 35S promoter driving GUS expression have been used as a comparison with the expression seen in the three different transformed plants showing the full range of expression levels observed.

The data indicated that GUS activity was detectable 6 hours post wounding and had not peaked by day 6. This expression profile in transgenic plants is different for any other promoter isolated by elicitor treatment of suspension cultured cells or intact plant tissue, such as the PR1a, chs 8 pal and chitinase promoters described earlier. Apart from being rapidly induced and driving sustained expression of the GUS marker gene the IPCR AoPR1 promoter affords higher expression levels that those achieved using any other wound-inducible or 'defence' gene promoter.

These data show that the IPCR AoPR1 promoter is driving strong expression at wound sites in explanted tissue during the time period when transformation by Agrobacterium takes place and at the point when selection is applied in transformation experiments. The transgenic plants chosen to demonstrate the activity of the IPCR AoPR1 promoter show that its range of expression is comparable with the CaMV 35S promoter. At later times post wounding the IPCR AoPR1 promoter achieves routinely higher levels of gene expression when compared to the constitutive CaMV35S promoter (FIG. 8).

Example 6

Super-induction of IPCR AoPR1 promoter directed gene expression following the addition of salicylic acid The same plants assayed for wound induced expression of the GUS reporter enzyme were used in studies using the abiotic chemical inducer salicylic acid. Leaf disks with and without wounding were incubated in the presence and absence of 4 mM salicylic acid. The data showed the super-induction of GUS expression after incubating leaf disks on 4 mM salicylic acid for a period of two days (FIG. 9). Expression of the AoPR1 promoter is inducible by a combination of wounding and salicylate to levels of GUS activity much higher than that achieved using the CaMV35S promoter (FIG. 9).

These data clearly indicate that the AoPR1 promoter can be super-induced by salicylic acid thus facilitating the identification of transgenic tissue in shoots, seedlings and mature plant organs.

Example 7

Expression of the IPCR AoPR1 promoter to drive GUS gene expression in wound site callus and regenerating shoot primordia and established suspension cell cultures of *Nicotiana tabacum*

Leaf explants of tobacco are transformed by Agrobacterium at wound sites on a medium that encourages rapid shoot primordia formation from wound callus as described by [Draper J, Scott R, Armitage P, Walden R: Plant Genetic Transformation and Gene Expression a Laboratory Manual, Blackwell Scientific Publications, Oxford (1988)]. The IPCR AoPR1 GUS expression was monitored during callus formation and shoot regeneration using a histochemical staining method for GUS activity [Draper et al., supra] and fluorometric analysis of GUS activity driven by the IPCR AoPR1 promoter showed that it was strongly expressed in wound-site derived callus and in callus regenerating shoot primordia on tobacco leaf explants placed on the shoot regeneration medium MSD4×2 and in established suspension cultured cells initiated from transformed callus. These data indicate that the IPCR AoPR1 promoter will be ideal for expressing marker genes in the required cell types in the majority of plant transformation protocols.

Example 8

Use of the AoPR1 promoter to control expression of the marker gene β-glucuronidase (GUS) in plant transformation experiments The data in Example 7 suggest that the IPCR AoPR1 promoter is active in the appropriate plant cells identified above as target cells in which marker gene expression was required during the plant transformation process by Agrobacterium. An Agrobacterium binary transformation vector was therefore constructed to allow the IPCR AoPR1 promoter to drive the expression of a marker gene during the required stages of Agrobacterium-mediated transformation of tobacco leaf explants. This vector contained the IPCR AoPR1 promoter fused to the reporter gene GUS. The 5'non-coding region of the GUS gene used was altered to remove the bacterial ribosome binding site and thus give minimal expression in Agrobacterium allowing easy recognition of transformed plant cells.

Since this gene fusion still gave low level expression in bacterial cells, an additional gene fusion between the IPCR AoPR1 promoter and a GUS gene containing an intron was also constructed which gave absolutely no expression in bacterial cells.

a) Construction of the AoPR1 transcriptional fusion intermediate vector

Two PCR primers, PAoPR1 1 with the sequence
5' CCGGTACCCTCAGGACTAGACC 3' (SEQ ID No:3)
and PAoPR1 2 with the sequence
3' GTAGCCACGATGTATTGGCGCCGACGTCGG 5' (SEQ ID No:3)
were synthesised. These primers were designed such that they were homologous to the AoPR1 promoter sequence (see FIG. 5) but included additional non-homologous sequence (shown in italics) which contained convenient restriction sites. These restriction sites allowed easy cloning of the AoPR1 promoter including the transcriptional start site but lacking any coding region (FIG. 11). A standard PCR reaction (see Example 3) was performed using these primers and the vector pSK(-) IPCR AoPR1 as the template. The resulting 900 bp PCR product (PCR-AoPR1) was digested with KpnI and PstI and cloned into KpnI/PstI-cut pJIT 60 to produce the vector pJIT-AoPR1 (FIG. 11).

b) Construction of a transcriptional fusion between the PCR-AoPR1 promoter and a GUS marker gene lacking a bacterial ribosome binding site The GUS gene lacking a bacterial ribosome binding site (GUS minus S/D) was obtained by digesting the vector pKIWI 105 (B-J. Janssen and R. C. Gardner (1990) Localised transient expression of GUS in leaf discs following cocultivation with Agrobacterium. *Plant Molecular Biology*, Vol. 14, 61–72) with SalI and EcoRI. The 2 kb SalI-EcoRI GUS encoding fragment was then cloned into SalI/EcoRI-cut pJIT-AoPR1 to produce pJIT-AoPR1-GUS (FIG. 12A). The entire expression cassette (i.e. PCR-AoPR1 promoter, GUS gene and CaMV polyadenylation signal) was isolated from pJIT-AoPR1-GUS by digestion with KpnI and XhoI. This 3.7 kb KpnI-XhoI fragment was then cloned into KpnI/SalI-cut pBIN 19 [Draper et al., supra] to produce the binary vector used in the transformation studies pBIN-AoPR1-GUS (FIG. 12A).

c) The construction of a gene fusion between the IPCR AoPR1 promoter and a GUS gene containing an intron The plasmid p35S GUS INT was kindly provided by Prof. Lothar Willmitzer (Berlin) and contains a plant intron within the coding region of the GUS gene (Vancanneyt et al, (1990) Construction of an intron-containing marker gene, *Molecular and General Genetics* 220 245–250). To allow cloning of the GUS INT gene downstream of the AoPR1 promoter, p35S GUS INT was digested with SstI, end filled by T4 DNA polymerase I and finally digested with BamHI. The 2 kb BamHI-SstI end filled GUS INT encoding fragment was then cloned into BamHI-SmaI digested pBluescript SK(-). The resulting plasmid was then digested with BamHI and EcoRI and the GUS INT gene cloned into BamHI-EcoRI digested pJIT-AoPR1 to produce pJIT-AoPR1-GUS INT (FIG. 12B). The entire expression cassette ie IPCR-AoPR1 promoter, GUS gene and CaMV polyadenylation signal was then isolated from pJIT-AoPR1-GUS INT by digestion with KpnI and XhoI. The resulting 3.7 kb KpnI-XhoI fragment was then cloned into KpnI-SalI-digested pBin19 (Bevan, 1984), to produce the binary vector used in the transformation studies pBin-AoPR1-GUS INT.

d) The expression of the PCR-AoPR1 GUS (minus S/D) and pBin-AoPR1-GUS marker genes can be used to monitor transformation events following inoculation of tobacco leaf explants with Agrobacterium The pBIN-AoPR1-GUS and pBin-AoPR1-GUS vectors was used to investigate the expression of the AoPR1 promoter during standard Agrobacterium-mediated transformation of tobacco leaf discs. The expression of GUS under the AoPR1 promoter was investigated by histochemical and fluorometric assays at various time points during the transformation procedure (FIG. 10). It was found that from as early as 3 days post inoculation, GUS activity was localised to the cut edges of explants and to the developing callus. The frequency of transformation, as indicated by the number of GUS-positive microcalli, in individual leaf explants was greater than, or at least equivalent to, that achieved using promoters such as those contained in the p35S GUS INT or pKIWI 105 vectors. GUS activity continued to be detected in callus tissue and small shoots and in the roots of shoots growing on rooting medium. After rooting had taken place very little GUS activity was detected in the developing leaves of small plantlets or in larger plants developing from these shoots. In quantitative terms, plants transformed by the IPCR AoPR1 GUS marker gene showed a range of marker gene expression that was 3–4 orders of magnitude lower than that found in transgenic plants (FIG. 13) harbouring markers genes driven by constitutive promoters such as CaMV35S (plasmid pBI121).

These experiments demonstrate that the AoPR1 promoter is active during those stages of the transformation procedure during which antibiotic selection must be applied. They also demonstrate that only minimal marker gene expression driven by the AoPR1 promoter is found in mature plants.

Example 9

The AoPR1 promoter can be used to express marker genes which may improve plant transformation efficiency. Transformation results in the generation of mature transgenic plants that exhibit minimal expression of selection marker genes and may have a minimal copy number of T-DNA inserts.

Expression of the neomycin phosphotransferase gene (npt-II) under the control of the constitutive CaMV 35S or nopaline synthase plant promoters is commonly used to confer resistance to the antibiotic kanamycin in plant transformation experiments. Similarly the expression of the pat gene encoding resistance to the herbicide BASTA™ is common used as a selective phenotype for the transformation of monocot cells. These resistance genes allow the selection of the resistant and therefore transformed plant tissue from those which are not transformed. Thus the PCR AoPR1 promoter can be used to express antibiotic and herbicide resistance genes and hence allow the selection of transformed plants.

a) Construction of a binary vector to allow the expression of npt-II under the control of the PCR AoPR1 promoter A 1 kb BamHI fragment encoding the npt-II gene was isolated from the vector pCaMVNeo and cloned into the BamHI site of pJIT-AoPR1 to produce the intermediate vector pJIT-AoPR1-Neo (FIG. 14). The pJIT-AoPR1-Neo plasmid was then linearised with XhoI and the entire plasmid including the expression cassette (i.e. AoPR1 promoter, npt-II gene and CaMV polyadenylation site) cloned into SalI-cut pSCV1 to produce the binary vector pSCV-AoPR1-NEO (FIG. 14).

b) Construction of a binary vector to allow the expression of pat under the control of the PCR AoPR1 promoter A 600 bp BamHI-EcoRI fragment encoding the pat gene which confers resistance to the herbicide BASTA™ was isolated from the vector pJIT 74 and cloned into BamHI/EcoRI-cut pJIT-AoPR1 to produce pJIT-AoPR1-PAT (FIG. 15). The 2.4 kb XhoI-KpnI fragment encoding the expression cassette (i.e. the AoPR1 promoter, pat gene and CaMV polyadenylation site) was then isolated from pJIT-AoPR1-PAT and cloned into KpnI/SalI-cut pBIN 19 to produce pBIN-AoPR1-PAT (FIG. 15).

c) The PCR AoPR1—NEO marker gene allows efficient recovery of transformed plants from tobacco leaf explants Experiments were performed using a standard Agrobacterium mediated transformation of tobacco leaf discs as described by Draper et al., supra. Similar procedures were used to transform potato leaf discs. The frequency of transformation observed in individual leaf explants was greater than, or at least equivalent to, that achieved using either the CaMV35S promoter or the mannopine synthase promoter (Table 16). Very little NPT-II activity could be detected in mature AoPR1-NPT-II-transformed tobacco plants using the dot blot assay described by Draper et al., supra.

TABLE 2

Tobacco

Frequency of kanamycin resistant calli and shoot formation from tobacco leaf disc explants inoculated with *A. tumefaciens* containing the 35S-NPT-II and AoPR1-NPT-II constructs, and root development on regenerated shoots in the presence of kanamycin.

| Construct | No. of individual[1] calli/ leaf disc ± SE | No. of regenerated[2] shoots/ leaf disc ± SE | % Rooting[3] shoots ± SE | No. of roots[3]/ shoot ± SE |
|---|---|---|---|---|
| 35S-NPT-II | 11.46 ± 0.8 | 4.80 ± 0.5 | 50 ± 17.6 | 4.8 ± 1.0 |
| AoPR1-NPT-II | 12.96 ± 1.1 | 5.37 ± 0.6 | 45 ± 13.4 | 5.6 ± 0.6 |

SE: Standard Error
[1]Two weeks after inoculation
[2]Four weeks after inoculation
[3]Two weeks after culture initiation Potato Frequency of kanamycin resistant shoot formation from potato leaf piece explants inoculated with *A. tumefaciens* containing binary vectors harbouring either the 3S-NPT-II or the AoPR1-NPT-II constructions after one month of selection on 100 mg/l kanamycin.

| Construct | % leaf pieces responding ± SE | No. of regenerated shoots/leaf pieces[4] ± SE |
|---|---|---|
| 35S-NPTII | 33.8 ± 5.6 | 2.50 ± 0.2 |
| AoPR1-NPTII | 31.9 ± 6.7 | 2.57 ± 0.3 |

[4]From leaf pieces which regenerated shoots d) Use of the PCR AoPR1—NEO marker gene allows efficient transformation in a range of dicotyledonous species Transformation experiments can be repeated with other plant species (eg Arabidopsis, potato, *Brassica napus*, pea and carrot) using appropriate transformation systems that incorporated a variety of explants which included cotyledons, petioles, leaf sections, roots, suspension cultured cells and protoplasts. In all cases transformation is achieved at levels equivalent to or greater than that achieved using constitutive promoters such as the CaMV35S promoter or the mannopine synthase promoter. In all transformants a very minimal expression of the marker genes is observed as compared to transformants derived using constitutively expressed marker genes. In all plants the minimal level expression of the marker gene does not effect the expression of any passenger genes (eg. GUS or NPT-II driven by different constitutive promoters). The populations of transgenic plants produced contained a lower copy number of T-DNA inserts than transformants generated using constitutive marker genes. This data demonstrated conclusively that the PCR AoPR1 promoter could be used to achieve the efficient generation of transformed shoots in several plant species and also shows that transformed plants can be generated which express the minimal amount of unwanted genetic information in mature plants and seedlings and may contain a minimal number of T-DNA inserts.

e) The PCR AoPR1 PAT gene can be used to efficiently transform monocot cell cultures Maize and Lollium suspension cell cultures were transformed using the microprojectile procedure of Klein, T., Kornstein, L., Sanford, J. C. and Fromm, M. E. (1989) Genetic transformation of maize cells by particle bombardment. *Plant Physiol.* 91:440–444. Transformation efficiency was superior or equal to that obtained using other marker genes driven by promoters not specifically designed to express in monocot suspension cultured cells and callus. Transformation efficiency may be further improved by modifying the promoter using enhancer elements, as described in the literature for other promoters (eg Last et al, *Theor. Appl. Genet.* 81 581–588 (1991)).

This information demonstrates the utility of the AoPR1 promoter in the development of transformation systems for cereals.

Example 10

The preferential expression of the IPCR AoPR1 promoter in tissue cultures can be exploited to express DNA coding for enzymes of industrial or commercial interest in undifferentiated plant cells. High levels of product are obtained in plant cell cultures.

The IPCR AoPR1 promoter is used to drive the expression of a gene which directly or indirectly results in the production of commercially useful compounds in plant cell culture. The gene product is targeted outside the cell and into the tissue culture medium by the addition of a suitable transit peptide. The level of expression of the gene and hence the amount of product recovered can be enhanced by the addition of salicylic acid. The product may be an enzyme or be any product changed in quantity or quality by the effect of preferential expression of the promoter in tissue cultures. Salicylic acid may be replaced by other compounds which super-induce the AoPR1 promoter eg other benzoic acid derivatives or microbial elicitors.

Examples of plant cell cultures and products of which the industrial applicability may be thus improved are:

| Plant cell culture | Product |
| --- | --- |
| *Digitalis lanata* | Digoxin |
| *Coleus blumei* | Rosmarinic acid |
| *Geranium spp* | Geraniol |
| *Raphanus spp* | Peroxidase |
| *Coptis japonica* | Berberine |
| *Iris spp* | Irone |
| *Panax ginseng* | Ginseng Biomass |
| *Taxus brevifolia* | Taxol |
| *Catharanthus roseus* | Catharanthine |
| *Lithospermum erythrorhizon* | Shikonin |

In addition, AOPR1-driven genes coding for commercially useful enzymes may be introduced into plant cells of species where cell proliferation is optimised (eg *N. tabacum*), thus providing an improved means of production of the enzymes and their products. The level of product may be enhanced further by the addition of salicylic acid to the growth medium. Examples of compounds currently produced in other systems (bacteria, yeast) which may be suitable for such production i plant cells are: leuenkephalin, human serum albumin, IgG, interleukins and other anti-cancer compounds, hepatitis-B virus antigens, interferon, and coagulation factors.

What is claimed is:

1. An isolated DNA molecule or an isolated recombinant DNA molecule, comprising a promoter which is expressed preferentially in callus cells and which promoter naturally drives expression of a gene encoding a predicted 16.92 kDa protein of *Asparagus officinalis* as shown in SEQ ID No. 7 or an equivalent plant protein derived from members of the Liliaceae or Amaryllidaceae.

2. A DNA molecule as claimed in claim 1, comprising a sequence upstream of the coding region shown in SEQ ID No. 7 nucleotide numbers 1 to 1041.

3. An isolated DNA molecule or an isolated recombinant DNA molecule, comprising a promoter which is expressed preferentially in callus cells and which promoter naturally drives expression of a gene encoding a predicted 16.92 kDa protein of *Asparagus officinalis* as shown in SEQ ID No. 7 or an equivalent plant protein derived from members of the Liliaceae of Amaryllidaceae, wherein said promoter is operatively linked to marker DNA which, when expressed, allows selection of, and/or screening for, transformed plant material.

4. A DNA molecule as claimed in claim 3, wherein the marker DNA codes for antibiotic resistance.

5. A DNA molecule as claimed in claim 4, wherein the marker DNA codes for aminoglycoside antibiotic resistance.

6. A DNA molecule as claimed in claim 3, wherein the marker DNA codes for herbicide resistance.

7. A DNA molecule as claimed in claim 6, wherein the marker DNA codes for phosphinothricin resistance.

8. A DNA molecule as claimed in claim 3, wherein the marker DNA codes for an enzyme.

9. A DNA molecule as claimed in claim 8, wherein the marker DNA codes for Beta-glucuronidase, chloramphenicol acetyl transferase (CAT) or luciferase.

10. A DNA molecule as claimed in claim 3, further comprising a 3' transcription regulation sequence.

11. A DNA molecule as claimed in claim 10, wherein the 3' transcription regulation signal is derived from the Cauliflower Mosaic Virus 35S gene.

12. An isolated DNA molecule or an isolated recombinant DNA molecule, comprising a promoter which is expressed preferentially in callus cells and which promoter naturally drives expression of a gene encoding a predicted 16.92 kDa protein of *Asparagus officinalis* as shown in SEQ ID No. 7 or an equivalent plant protein derived from members of the Liliaceae or Amaryllidaceae, wherein said promoter is operatively linked to DNA involved in the production of a substance sought to be recovered from a plant cell or tissue culture.

13. A DNA molecule as claimed in claim 12, wherein said substance is a protein encoded by the DNA linked to the promoter.

14. A DNA molecule as claimed in claim 12, wherein an enzyme, encoded by the DNA linked to the promoter, is involved in the production of said substance.

15. A vector comprising an isolated DNA molecule or an isolated recombinant DNA molecule, comprising a promoter which is expressed preferentially in callus cells and which promoter naturally drives expression of a gene encoding a predicted 16.92 kDa protein of *Asparagus officinalis* as shown in SEQ ID No. 7 or an equivalent plant protein derived from members of the Liliaceae or Amaryllidaceae, wherein said promoter is operatively linked to marker DNA which, when expressed, allows selection of, and/or screening for, transformed plant material.

16. A vector as claimed in claim 15, which is a disarmed Ti-plasmid vector.

17. A host cell transfected or transformed with a vector comprising an isolated DNA molecule or an isolated recombinant DNA molecule, comprising a promoter which is expressed preferentially in callus cells and which promoter naturally drives expression of a gene encoding a predicted 16.92 kDa protein of *Asparagus officinalis* as shown in SEQ ID No. 7 or an equivalent plant protein derived from members of the Liliaceae or Amaryllidaceae, wherein said promoter is operatively linked to marker DNA which, when expressed, allows selection of, and/or screening for, transformed plant material.

18. A host cell as claimed in claim 17, which is an Agrobacterium cell.

19. A process for preparing a DNA molecule as claimed in any one of claims 1, 3, or 12, comprising coupling together successive nucleotides, and/or ligating oligo- and/or poly-nucleotides.

20. A process for preparing a transformed plant cell, the process comprising introducing DNA as claimed in any one of claims 1, 3, or 12 into the plant cell.

21. A cell or tissue culture of a monocotyledon or dicotyledon transformed with DNA as claimed in any one of claims 1, 3, or 12.

22. A transgenic plant, or part thereof, comprising DNA as claimed in any one of claims 1, 3, or 12.

23. Propagating material of a transgenic plant as claimed in claim 22.

* * * * *

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: misc_feature
      (B) LOCATION: 1..20
      (D) OTHER INFORMATION: /product= "EXT.1 PRIMER"

(xi) SEQUENCE DESCRIPTION: SEQ ID NO: 1:

CGAGGTTGTG CCAGTCGAGC          20

(2) INFORMATION FOR SEQ ID NO: 2:

(i) SEQUENCE CHARACTERISTICS:
      (A) LENGTH: 20 base pairs
      (B) TYPE: nucleic acid
      (C) STRANDEDNESS: single (D) TOPOLOGY: linear (ii) MOLECULE TYPE: cDNA (ix) FEATURE:
        (A) NAME/KEY: misc_feature
        (B) LOCATION: 1..20
        (D) OTHER INFORMATION: /product= "IPCR 1 PRIMER"

(xi) SEQUENCE DESCRIPTION: SEQ ID NO: 2:

GCCTGACTTT ATTGCCGGTG                                                    20

(2) INFORMATION FOR SEQ ID NO: 3:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..22
        (D) OTHER INFORMATION: /product= "PAoPR1 1 PRIMER"

(xi) SEQUENCE DESCRIPTION: SEQ ID NO: 3:

CCGGTACCCT CAGGACTAGA CC                                                 22

(2) INFORMATION FOR SEQ ID NO: 4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..30
        (D) OTHER INFORMATION: /product= "PAoPR1 2 PRIMER"

(xi) SEQUENCE DESCRIPTION: SEQ ID NO: 4:

GTAGCCACGA TGTATTGGCG CCGACGTCGG                                          30

(2) INFORMATION FOR SEQ ID NO: 5:

(i) SEQUENCE CHARACTERISTICS:
        (A) LENGTH: 737 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..477

(xi) SEQUENCE DESCRIPTION: SEQ ID NO: 5:

ATG AGT TCA GGG AGC TGG AGC CAC GAG GTC GCT GTC AAT GTC GCC GCA          48
Met Ser Ser Gly Ser Trp Ser His Glu Val Ala Val Asn Val Ala Ala
 1               5                  10                  15

GGA CGG ATG TTC AAG GCG GCA ATG CTC GAC TGG CAC AAC CTC GGC CCT          96
Gly Arg Met Phe Lys Ala Ala Met Leu Asp Trp His Asn Leu Gly Pro
                20                  25                  30

AAG ATT GTG CCT GAC TTT ATT GCC GGT GGC TCA GTG GTG TCT GGA GAT         144

```
Lys Ile Val Pro Asp Phe Ile Ala Gly Gly Ser Val Val Ser Gly Asp
              35                  40                  45

GGA TCT GTA GGA ACC ATC CGA GAG ATC AAG ATC AAC AAT CCT GCT ATA       192
Gly Ser Val Gly Thr Ile Arg Glu Ile Lys Ile Asn Asn Pro Ala Ile
 50                  55                  60

CCT TTC AGC TAT GTG AAG GAA CGC CTG GAT TTC GTA GAC CAT GAC AAG       240
Pro Phe Ser Tyr Val Lys Glu Arg Leu Asp Phe Val Asp His Asp Lys
 65                  70                  75                  80

TTC GAG GTG AAG CAG ACC CTC GTG GAA GGT GGA GGT TTA GGT AAG ATG       288
Phe Glu Val Lys Gln Thr Leu Val Glu Gly Gly Gly Leu Gly Lys Met
                 85                  90                  95

TTT GAA TGT GCC ACC ACT CAC TTC AAG TTC GAG CCC TCG AGC AAC GGT       336
Phe Glu Cys Ala Thr Thr His Phe Lys Phe Glu Pro Ser Ser Asn Gly
                 100                 105                 110

GGA TGC CTC GTC AAG GTG ACT GCA TCC TAC AAG ATT CTC CCA GGT GTC       384
Gly Cys Leu Val Lys Val Thr Ala Ser Tyr Lys Ile Leu Pro Gly Val
                 115                 120                 125

GCC GAT GAG AGT GCG AAG GCG AAG GAG GGA ATA ACC AAC CAC ATG AAG       432
Ala Asp Glu Ser Ala Lys Ala Lys Glu Gly Ile Thr Asn His Met Lys
130                 135                 140

GCA ACC GAA GCT TAC CTC CTA GCC AAC CCA ACT GCC TAC GTT TAAATATAGT    484
Ala Thr Glu Ala Tyr Leu Leu Ala Asn Pro Thr Ala Tyr Val
145                 150                 155

GATTGTGTTT CTTTGCGTGA AGTGCTTGTG AGTTTGAATA AGGAGATTGG TTATGAGGAA    544

GCTTGATGGG GTCATACATA GTTAGTTTAT GTTGAATGAT CAGCCTTTTT TGTGTGAAGT    604

ACTTGGGAGT TTGAATAAGG AGACTGAATA TGAGAAAGAT TGATGGAGTT ATCGTTCATG    664

TTGAATGATC AGCCTTATCA GTTTGTAACA GTGTCGAATG ATCAGTCTTA TCAGTTTGTA    724

ATGGTGGCTT CAA                                                      737

(2) INFORMATION FOR SEQ ID NO: 6:

(i) SEQUENCE CHARACTERISTICS:
        (A) LENGTH: 158 amino acids
        (B) TYPE: amino acid
        (D) TOPOLOGY: linear (ii) MOLECULE TYPE: protein (xi) SEQUENCE DESCRIPTION: SEQ ID NO: 6:

Met Ser Ser Gly Ser Trp Ser His Glu Val Ala Val Asn Val Ala Ala
 1               5                  10                  15

Gly Arg Met Phe Lys Ala Ala Met Leu Asp Trp His Asn Leu Gly Pro
                 20                  25                  30

Lys Ile Val Pro Asp Phe Ile Ala Gly Gly Ser Val Val Ser Gly Asp
                 35                  40                  45

Gly Ser Val Gly Thr Ile Arg Glu Ile Lys Ile Asn Asn Pro Ala Ile
 50                  55                  60

Pro Phe Ser Tyr Val Lys Glu Arg Leu Asp Phe Val Asp His Asp Lys
 65                  70                  75                  80

Phe Glu Val Lys Gln Thr Leu Val Glu Gly Gly Gly Leu Gly Lys Met
                 85                  90                  95

Phe Glu Cys Ala Thr Thr His Phe Lys Phe Glu Pro Ser Ser Asn Gly
                 100                 105                 110

Gly Cys Leu Val Lys Val Thr Ala Ser Tyr Lys Ile Leu Pro Gly Val
                 115                 120                 125

Ala Asp Glu Ser Ala Lys Ala Lys Glu Gly Ile Thr Asn His Met Lys
130                 135                 140
```

Ala Thr Glu Ala Tyr Leu Leu Ala Asn Pro Thr Ala Tyr Val
145                 150                 155

(2) INFORMATION FOR SEQ ID NO: 7:

(i) SEQUENCE CHARACTERISTICS:
        (A) LENGTH: 1132 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1042..1132

(xi) SEQUENCE DESCRIPTION: SEQ ID NO: 7:

| | | | | | |
|---|---|---|---|---|---|
| GAATTCAGGG | GTAAGTTTGC | AAATATCAAG | ATTTGGGGGG | GCCAAATCTA | CAAATATGAA | 60 |
| ATATTTGAGA | GGTATGTATG | CAAAAACCCC | TATAAAATTT | CCCTCAGGAC | TAGACCATCG | 120 |
| TGGTTAAATG | ATCAAGTGCC | TACTTGGCAG | AATTTCTTTC | GAGCAGCCTC | CTCCTACAAG | 180 |
| TTGCATTTGT | TGCGCTTACG | ATAATTGTCA | AAGAAGTAGG | TAAAATAAAG | ACATGATCAC | 240 |
| TAATATTAAG | GATAAGATTA | AAAATAAGTC | CAGGATTAAC | CGGTCGGCCC | ATCAATTACT | 300 |
| TGCTGACCTT | TGTTGCCGTC | CCACGACTTC | CATTTTCTAA | CCGTCCATTT | TTCATTTGTT | 360 |
| TTTAGCTATA | TTTAATATTA | ATGGGATATA | AATTATAAAC | ATTCCTCCTC | CCAAAAAAAT | 420 |
| AAGTTTAAGT | AATACTGCAA | TAGACAGTGT | TTTAAGCCAT | GTAATTCAGT | AAAAGTTCTT | 480 |
| TTTTATTCTG | AACCTAGCCC | TAAAAAGGCC | ATGCGGGTAA | TTAGTTCAGT | CAACTGAATA | 540 |
| TACAACGTTT | TGAACCAAAG | TTAACATGTA | CAGGCCAATA | GAAGTTATTT | GACCGTAAGC | 600 |
| TTAGTCTCTA | CATTCATTCA | ACGTTCTTGA | ATCAAAGTGA | CCTGTACAGG | CCAATAGAAG | 660 |
| TTACCTGACC | GTAAGCTTAG | TCTCTACATT | CATTCCTCTG | AGACGATATT | CTAGAAGCCT | 720 |
| GCTTTCAAGT | CTAAAAGGCA | CAATCTTTTT | TCCTCACCAC | TTGTTGAGGT | ACTTATGATT | 780 |
| TTAAAGATGA | AACATTTTTT | TTACTTTTCC | CCTTTAATTT | CTTTGATTTT | TTTTTTTCTT | 840 |
| GGTAGTTGGA | AGTACTTTTC | ATACCCTAGA | AAATCCACTG | TTGATCTTTG | AAATATCAGC | 900 |
| AATCTTTGAA | ATAATATCAG | CAACCACGAC | ACCTACCATT | CTCAAATTCA | CTCTATAAAA | 960 |
| GGGTAAACCT | TTGCTTACCT | CTATGCTCAC | TCACAAGGAG | AACAAACACT | CATCGGTGCT | 1020 |

ACATAACAAC AGAGAGGAAA C ATG AGT TCA GGG AGC TGG AGC CAC GAG GTC        1071
                       Met Ser Ser Gly Ser Trp Ser His Glu Val
                         1               5                  10

GCT GCC AAT GTC GCC GCA GGA CGG ATG TTC AAG GCG GCA ATG CTC GAC        1119
Ala Ala Asn Val Ala Ala Gly Arg Met Phe Lys Ala Ala Met Leu Asp
             15                  20                  25

TGG CAC AAC CTC G                                                      1132
Trp His Asn Leu
            30

(2) INFORMATION FOR SEQ ID NO: 8:

(i) SEQUENCE CHARACTERISTICS:
        (A) LENGTH: 30 amino acids
        (B) TYPE: amino acid
        (D) TOPOLOGY: linear (ii) MOLECULE TYPE: protein (xi) SEQUENCE DESCRIPTION: SEQ ID NO: 8:

-continued

```
Met Ser Ser Gly Ser Trp Ser His Glu Val Ala Ala Asn Val Ala Ala
 1               5                  10                  15

Gly Arg Met Phe Lys Ala Ala Met Leu Asp Trp His Asn Leu
             20                  25                  30
```